United States Patent [19]

Torrisi et al.

[11] Patent Number: 4,974,244

[45] Date of Patent: Nov. 27, 1990

[54] SAMPLE POSITIONING METHOD AND SYSTEM FOR X-RAY SPECTROSCOPIC ANALYSIS

[75] Inventors: Angelo M. Torrisi, 10 Anpell Dr., N.Y. 10583; Roland Urbano, Tuckahoe, N.Y.

[73] Assignee: Angelo M. Torrisi, Scarsdale, N.Y.

[21] Appl. No.: 390,584

[22] Filed: Aug. 7, 1989

Related U.S. Application Data

[63] Continuation of Ser. No. 228,628, Aug. 4, 1988.

[51] Int. Cl.⁵ .......................................... G01N 23/223
[52] U.S. Cl. .......................................... 378/45; 378/83
[58] Field of Search ....................... 378/82, 83, 79, 45, 378/46, 49, 205

[56] References Cited

U.S. PATENT DOCUMENTS

| | | | |
|---|---|---|---|
| 4,037,109 | 7/1977 | Hosokawa et al. | 378/79 |
| 4,445,225 | 4/1984 | White | 378/44 |
| 4,448,311 | 5/1984 | Houser | 378/208 |
| 4,575,869 | 3/1986 | Torrisi et al. | 378/47 |
| 4,587,666 | 5/1986 | Torrisi et al. | 378/45 |
| 4,698,210 | 10/1987 | Solazzi | 378/79 |

Primary Examiner—Craig E. Church
Attorney, Agent, or Firm—Paul J. Sutton

[57] ABSTRACT

A method of positioning a sample for X-Ray spectroanalysis at a spectroscopic machine that includes the steps of determining the point of primary focus of an X-Ray beam upon a master grid and then placing the data upon a mating assembly grid that is positioned in an assembly well into which is positioned a grid support that carries the assembly grid with the primary focus point. Further steps include assembling a sample holder with one sheet of film in the assembly well. An interlocking member that locks the sample holder into interlocking relationship with both the grid support and the sample holder is then inserted into the well. The sample is then aligned upon the point of primary focus upon the film in the fixed sample holder. The sample holder is removed from engagement with the interlocking member and transferred to the sample holder support plate at the spectroscopic machine where the sample is aligned with the primary focus. The sample holder can be optionally mounted with two sheets of film sandwiching the sample at the well.

29 Claims, 18 Drawing Sheets

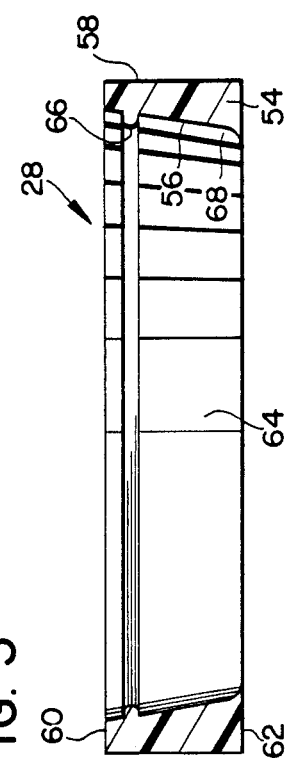
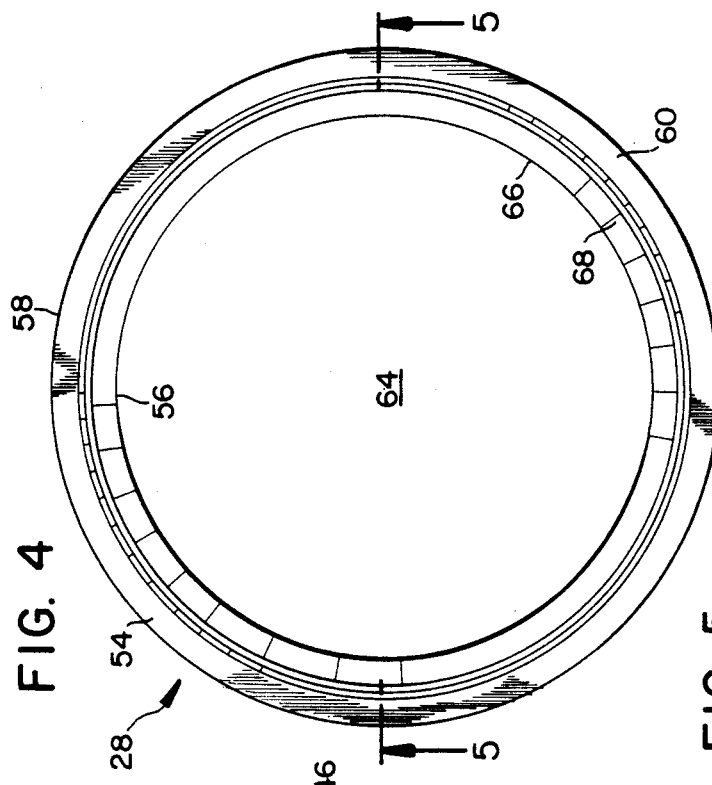
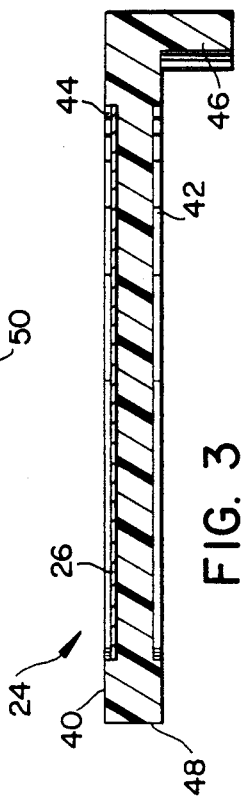
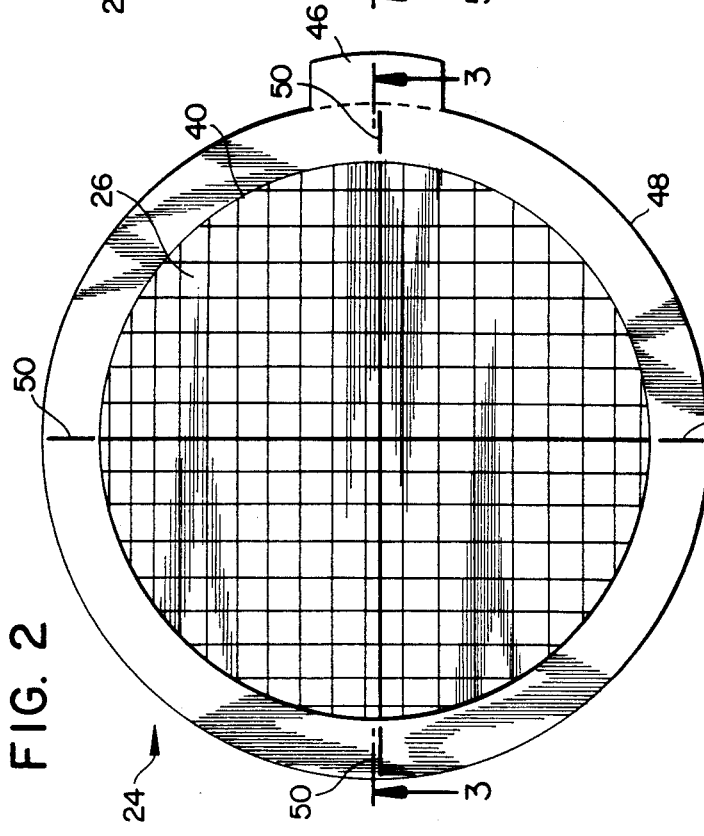

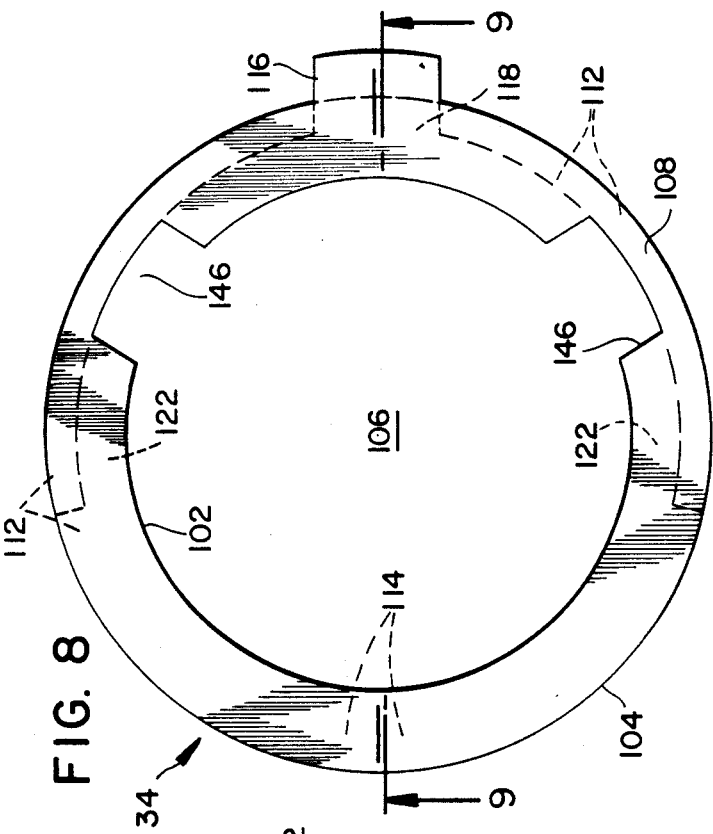
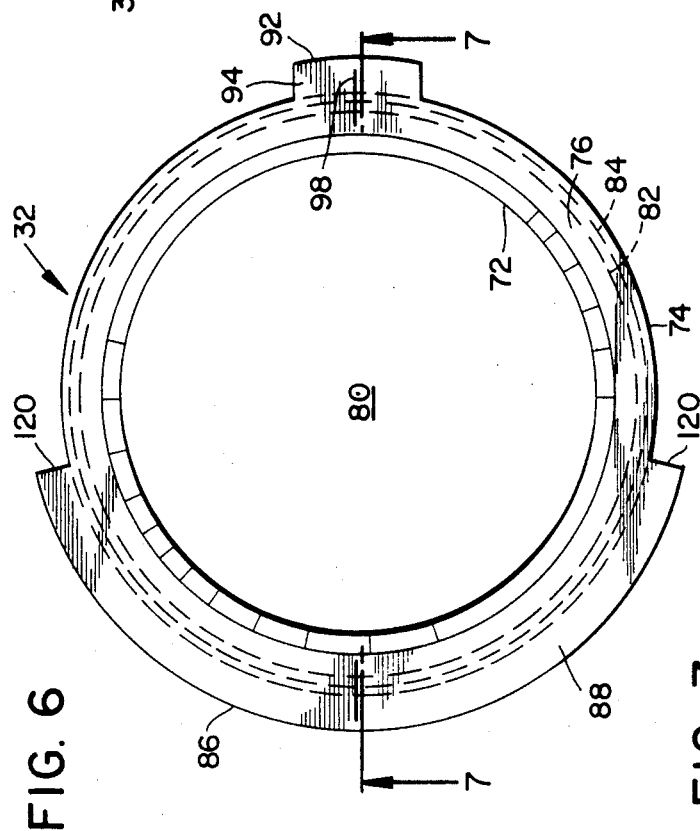
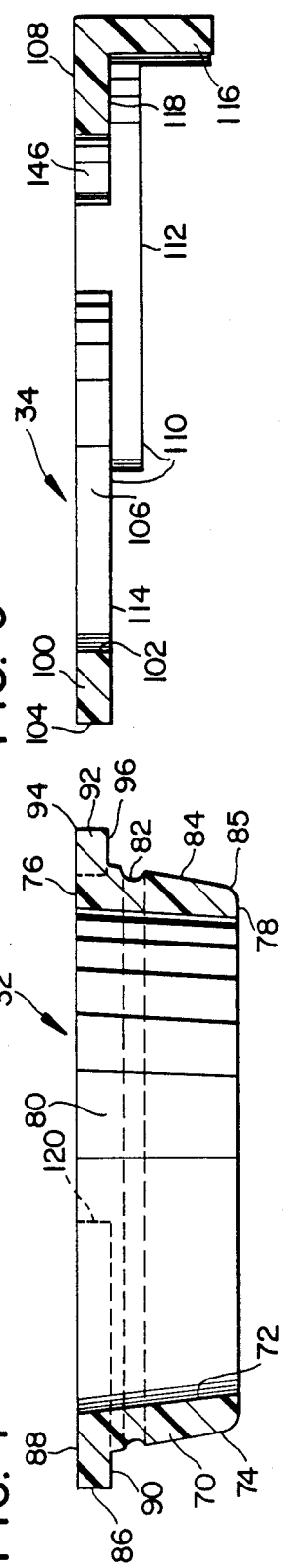

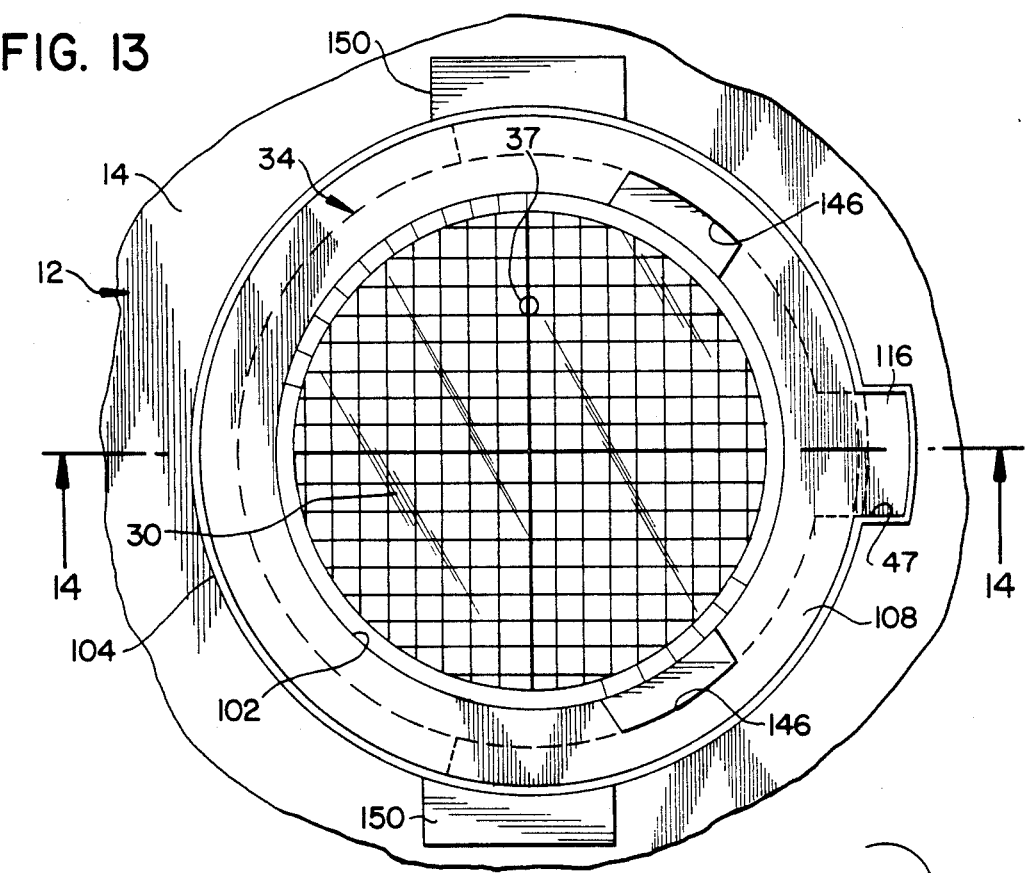
FIG. 13
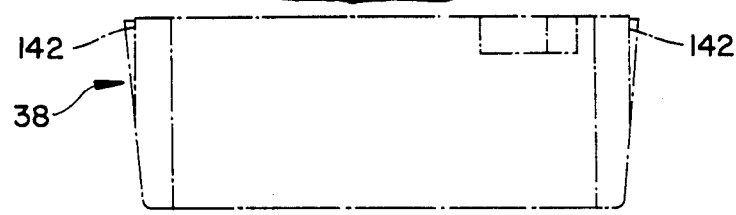
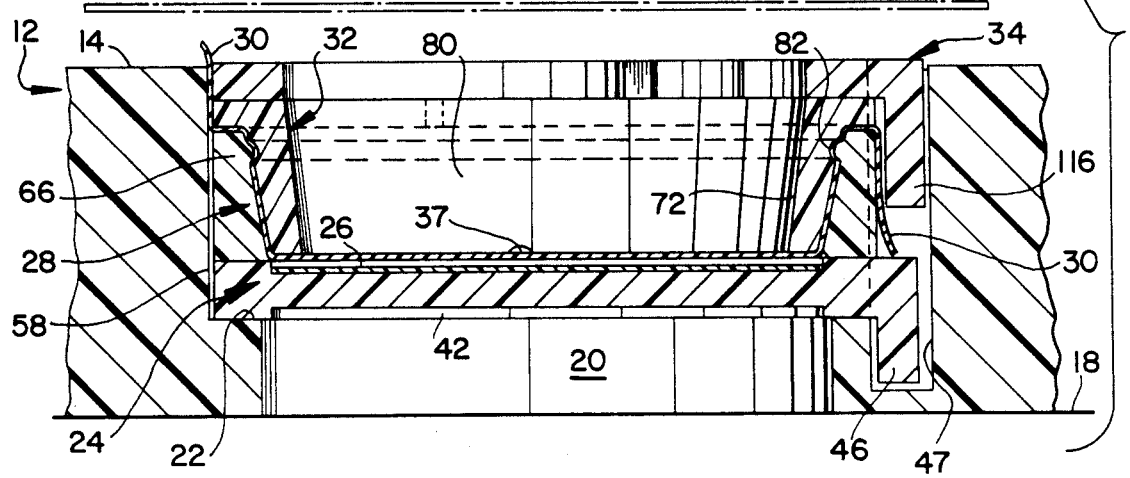
FIG. 14

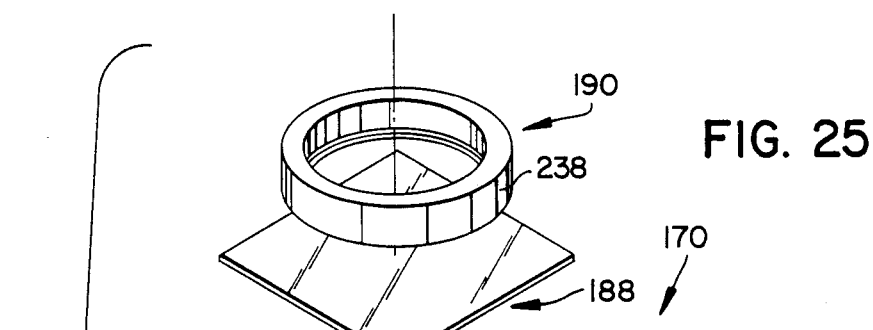
FIG. 25
FIG. 26
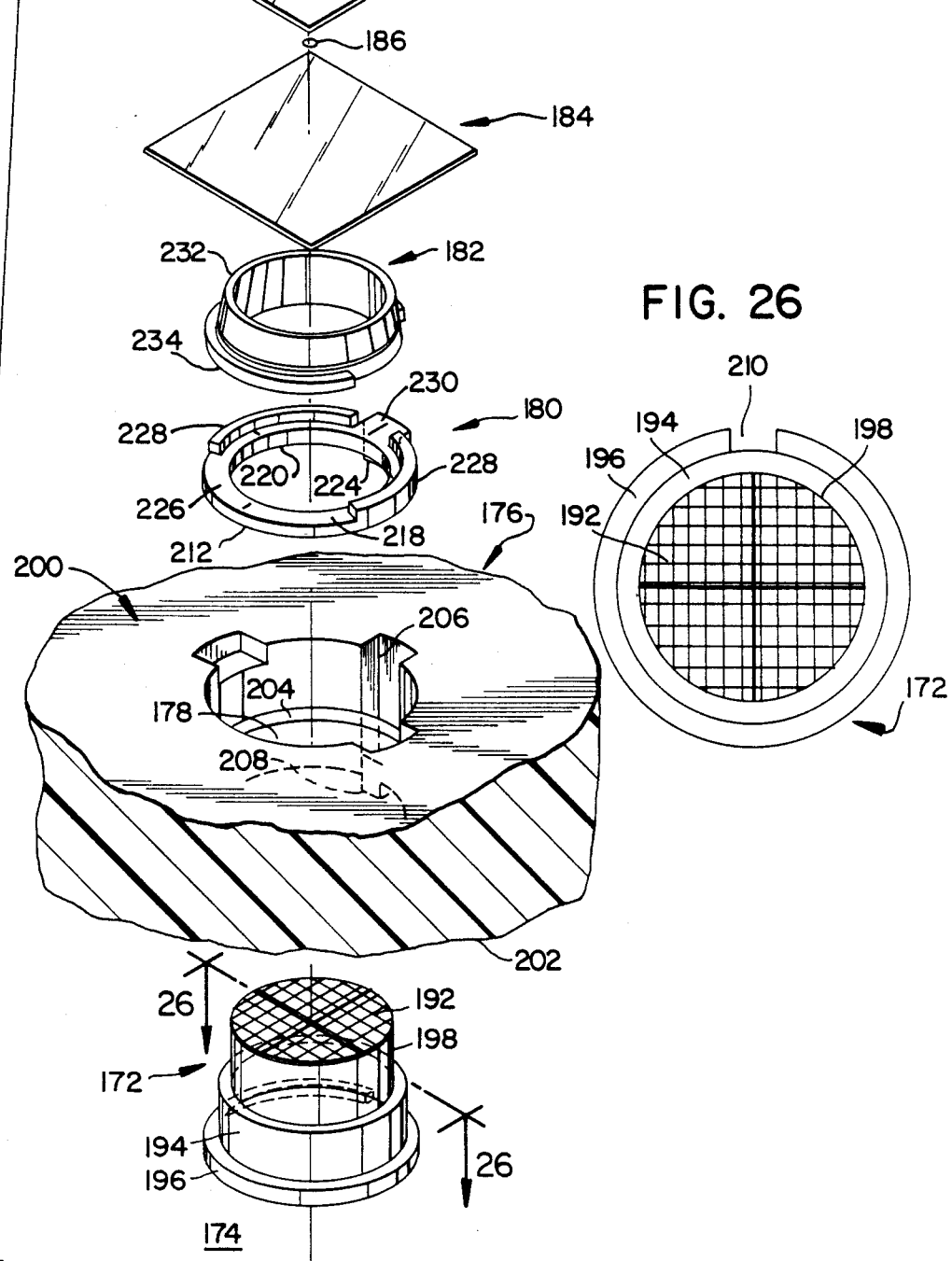

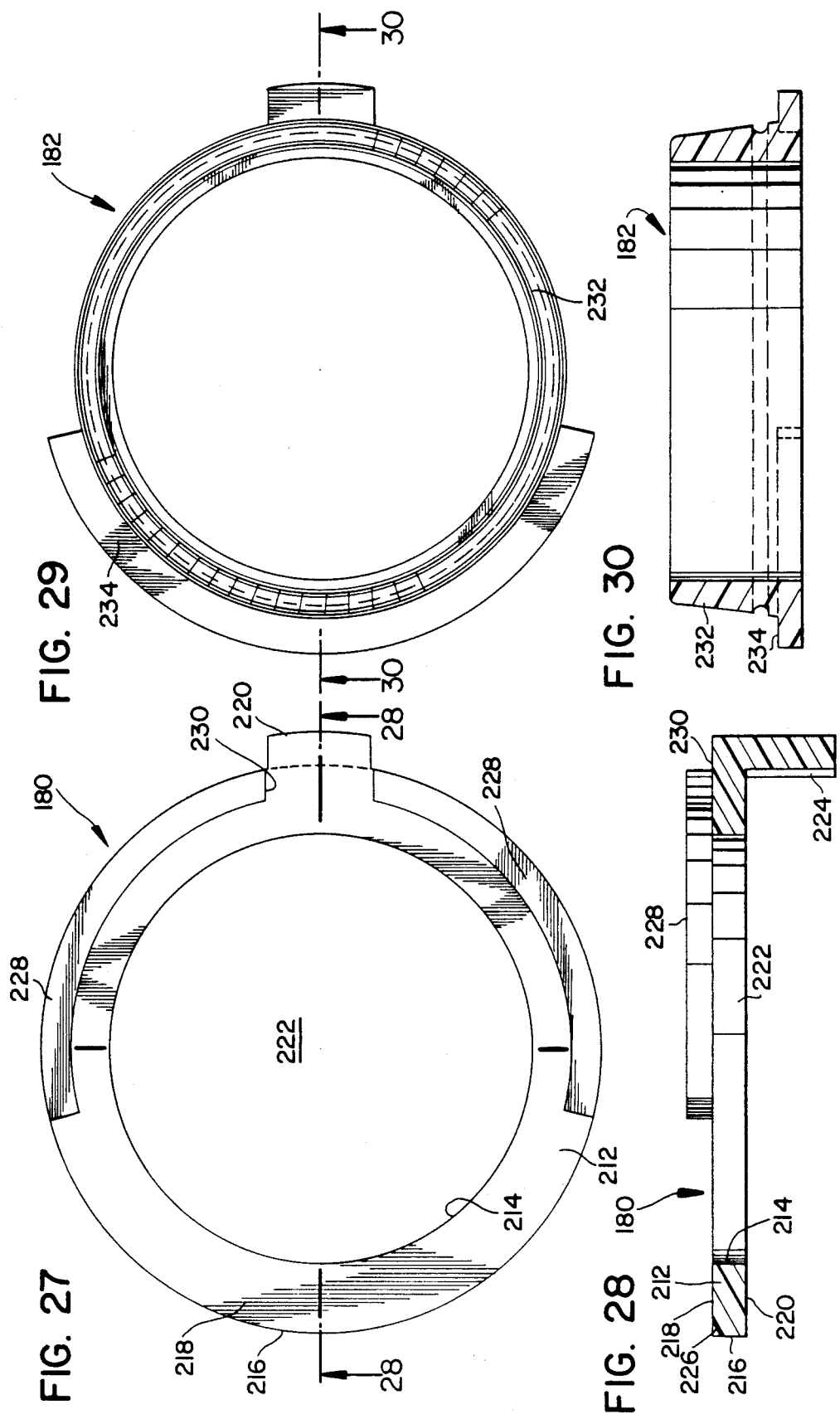

SAMPLE POSITIONING METHOD AND SYSTEM FOR X-RAY SPECTROSCOPIC ANALYSIS

This is a continuation of application Ser. No. 228,628 filed Aug. 4, 1988.

This application relates to a sample support for X-Ray spectroscopic analysis and more particularly to a sample support for thin film that precisely positions mini-/micro-samples for spectro-chemical analysis by X-Ray energy and wavelength dispersive systems.

BACKGROUND OF THE INVENTION

One problem in the X-Ray spectroscopic industry is precision positioning the sample to be analyzed in the sample holder so that the sample is repetitively and precisely aligned with the "hot spot", or point of primary focus, of the X-Ray spectrometer beam to assure reliable replicate analytical readings from sample to sample. Constant realigning of each batch of samples is necessary since the hot spot tends to drift slowly and irregularly around the area of the striking beam.

One method of sample alignment used in the spectroscopic industry at present is as follows. The analyst empirically determines the position of the hot spot by empirically reading the X-Ray energy output across the analytical sample area and marks the results of the empirical readings onto a grid. A number of data readings results in the ability to pinpoint X-Y readings onto the grid and leads to a final measurement of the hot spot. The sample holder with the sample is then placed on a grid and the sample is aligned with the data reading of the hot spot. The problem with this reading is that the sample holder can move slightly during the aligning process with the result that the possibility of human error is greatly increased with repeated positionings of analogous samples with the result that the scientific basis of the analysis can be questioned.

Another method of sample holder alignment used in the industry today is similar to the method just described, except that a 35 mm slide holder with a transparent film window is used. The slide holder is generally square and fits into a square recess under the beam of the X-Ray spectrometer. Slide-type sample holders, however, are not adapted to grip a film layers of film between which the sample is located in a firm and taut manner, with the result that the film layers tend to crease, or wrinkle, in a large percentage of cases. If a wrinkle shifts even slightly, the sample will be misaligned relative to the hot spot and the results of the reading will be faulty.

The scientific worth of an X-Ray spectroscopic analysis is based upon the capacity to obtain and duplicate results from sample to sample. For that, several factors have to be controlled. One of these factors is the ability to place the sample in the hot spot each time an analysis is made.

Yet another problem of the spectroscopic industry is that of interference with the primary X-Ray beam by rays reflected from the inner surface of the sample holder. This type of interference occurs because of the comparatively high walls of the sample holder, which reflect the rays that bypass the sample from below, pass to the sides of the walls, bounce around the inside of the holder and generally create a static or noise that can actually be reflected to the analyzer of the spectroscope so as to add background signals that tend to obscure the desired wavelengths.

What the industry needs is a system of obtaining reproducible values from the spectroscopic analysis of a sample by precisely positioning the sample in an optimum repetitive, or sample-to-sample, location along with a system that provides a stable environment for the mini-/micro-sample positioned between two layers of thin film that are flat and taut.

SUMMARY OF THE INVENTION

It is, therefore, an object of the present invention to provide a system and a method that overcomes the problems set forth above.

It is another object of the present invention to provide a system for accurately and repetitively positioning a mini-/micro-sample for spectroscopic analysis.

It is another object of the present invention to provide a system of mounting a mini-/micro-sample for spectroscopic analysis between two layers of thin film that do not crease or wrinkle so that the micro-sample will maintain a constant position in the sample holder.

It is yet another object of the present invention to provide a system for mounting a mini-/micro-sample between two layers of thin film that sandwich the sample and permit air pockets to be released in a vacuum or other environment, so that the mini-/micro-sample, which is aligned with the desired point of primary focus, will maintain its position at the point of primary focus.

It is another object of the present invention to provide a system for mounting a sample with one or two film layers for spectroscopic analysis in a sample holder that is fixed so that the sample will be correctly aligned with the hot spot at the spectroscope.

It is still another object of the present invention to provide a system for mounting a sample for spectroscopic analysis in a sample holder that minimizes interference of background disturbance of X-Ray beams.

In accordance with the above objects and other objects that will become apparent hereinafter, a method and a system of positioning a sample for X-Ray spectroscopic analysis at a spectroscopic machine comprising the following steps: (1) placing an assembly board having opposed top and bottom surfaces with the bottom surface upon a support surface, the board forming a generally upright well having an inner surface; (2) placing a grid support having an outer surface adapted to be slidingly received by the inner surface of the well means into the well means, which is for receiving the grid support, the grid support having a top side and an upwardly facing assembly grid, the grid support and the assembly board including keying elements adapted to retain the grid support in non-rotatable relationship with the assembly board and a support step extending into the well; (3) recording the point of primary focus data of the X-Ray beam onto a master grid; (4) translating the primary focus grid data at the master grid onto the assembly grid and marking the position thereon; (5) placing an interlocking member and a sample holder mounting at least one sheet of transparent film with a sample to be analyzed positioned in contact with the at least one film in the well, which is adapted to slidingly receive the interlocking member and the sample holder along the inner surface thereof, upon the grid support with the sample positioned over the assembly grid at the marked position of primary focus; the interlocking member is adapted to retain the sample holder in non-rotational relationship with the assembly board and with the grid support and the assembly grid; the support step at the well being adapted to bear at least the sample holder and the interlocking member; (6) separating the sample holder with the sample from its relationship with the interlocking member; (7) removing the sample holder with the sample from the well; and (8) placing the sample holder with the sample into position at the spectrometer supporting plate so that the sample is positioned at the point of primary focus.

The method outlined above can be adapted for one or two layers of film. The film can be very thin films.

The film or films in each case are pressed between two, or three, holder members which when mounted in locked relationship together form the sample holder. The sample holder is mounted, as described above, in the well, with the interlocking member locking the sample holder into non-rotational relationship in the well with the assembly board and with the likewise locked grid support and its assembly grid, the last two being locked, preferably by keying, but also by other means, with the assembly board. Only when the film is locked across the assembly grid is the sample set upon the film layer over the hot spot marked on the assembly grid. The interlocking member is adapted to be easily removed from the sample holder after the sample has been aligned with the hot spot.

The outer and inner holder members that comprise the sample holder include walls, preferably circular, that form aligning apertures. These walls, in fact the wall of the assembled sample holder, are are preferably low profile walls so that beams from the spectrometer will pass out of the sample holder leaving the beams reflected from the sample comparatively free from static.

BRIEF DESCRIPTION OF THE DRAWINGS

FIG. 2 is a top view of the grid support member of the sample positioning system shown in FIG. 1;

FIG. 3 is a view taken through line 3—3 of FIG. 2;

FIG. 4 is a top view of the outer holder member of the sample positioning system shown in FIG. 1;

FIG. 5 is a view taken along line 5—5 of FIG. 4;

FIG. 6 is a top view of the first inner holder member of the sample positioning system shown in FIG. 1;

FIG. 7 is a view taken along line 7—7 of FIG. 6;

FIG. 8 is top view of the interlocking member of the sample positioning system shown in FIG. 1;

FIG. 9 is a view taken along line 9—9 of FIG. 8;

FIG. 13 is a top view of the assembly system being assembled with the second inner holder member in a raised, non-assembled position and shown in phantom line;

FIG. 14 is a sectional view taken through line 14—14 of FIG. 13;

FIG. 25 is an exploded perspective view of another embodiment of the present invention;

FIG. 26 is a top view of the grid support taken through line 26—26 of FIG. 25;

FIG. 27 is a top view of the interlocking member shown in FIG. 25;

FIG. 28 is a sectional view taken through line 28—28 of FIG. 27;

FIG. 29 is a top view of the inner holder member shown in FIG. 25;

FIG. 30 is a sectional view taken through line 29—29 shown in FIG. 29;

DESCRIPTION OF THE PREFERRED EMBODIMENTS

Figure 1:
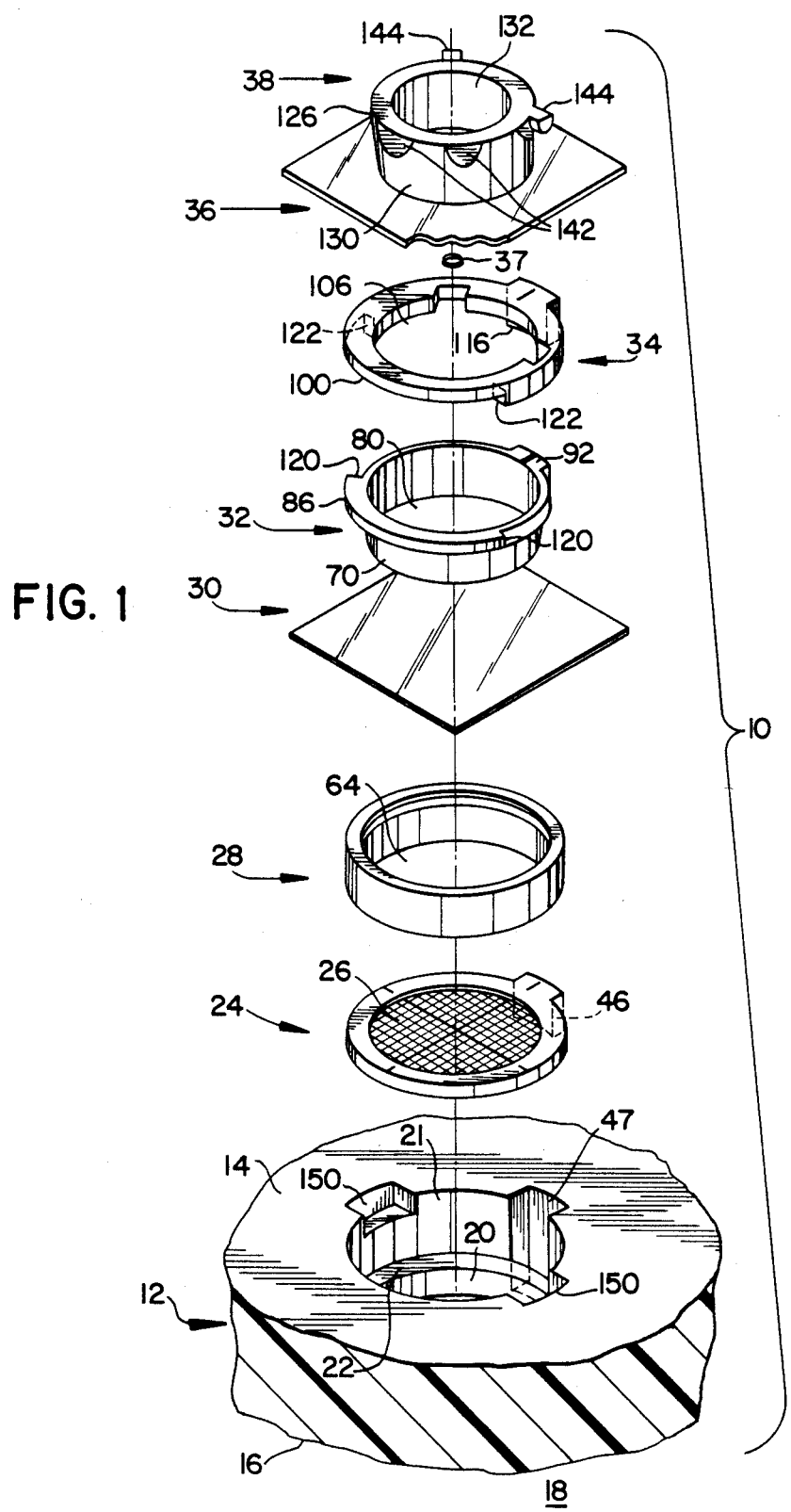
FIG. 1 is an exploded-type perspective view of the sample positioning system for two layers of film prior to mounting in the well of an assembly board.

Reference is now made in detail to the drawings in which identical or similar elements are designated by the same reference numerals throughout.

FIG. 1 shows a perspective view of a schematic rendering of a sample positioning system 10 in the process of being assembled. An assembly board 12 having opposed top and bottom surfaces 14 and 16, respectively, is placed upon a support surface 18, such as a table. A circular well 20 having a circular inner surface 21 is formed in assembly board 12 with a circular support step 22 spaced from top surface 14 extending from inner surface 21 into well 22 spaced.

A grid support 24, shown in detail in FIGS. 2 and 3, is shown ready for placement into well 20. Grid support 24 is configured as a plate-like member holding an assembly grid 26, which is analogous to a master grid at the spectroscopic X-Ray machine, which is shown in schematic representation in FIG. 27 and which will be discussed later.

A generally ring-shaped outer holder member 28, shown in detail in FIGS. 4 and 5, adapted to be slidingly received along circular inner surface 21 in well 20 is shown ready to be placed on top of grid support 24, which is adapted to directly bear outer holder member 28. A first sheet of transparent film 30 of a type known in the art of X-Ray spectroscopic analysis is shown ready for placement over well 20 and over outer holder member 28.

A generally ring-shaped inner holder member 32, which is shown in detail in FIGS. 6 and 7, is shown ready to be placed into well 20 and forced into a snap-fit locking engagement with outer holder member 28 along with first film 30, which will be gripped between outer and inner holder members 28 and 32 so as to create a taut surface across the members in a manner to be explained in detail below.

Next, a generally ring-shaped interlocking member 34, which is shown in detail in FIGS. 8 and 9, is shown ready for placement into well 20 over outer and inner holder members 28 and 32. As will be explained below, interlocking member is adapted to be retained in well 20 in non-rotatable relationship with assembly board 12 and is further adapted to retain inner holder member 32 in non-rotational relationship with itself and thus with assembly board 12.

Next, a sample 37 destined for X-Ray chemical analysis under the spectroscopic machine is shown ready for placement upon first film 30.

Figure 10:
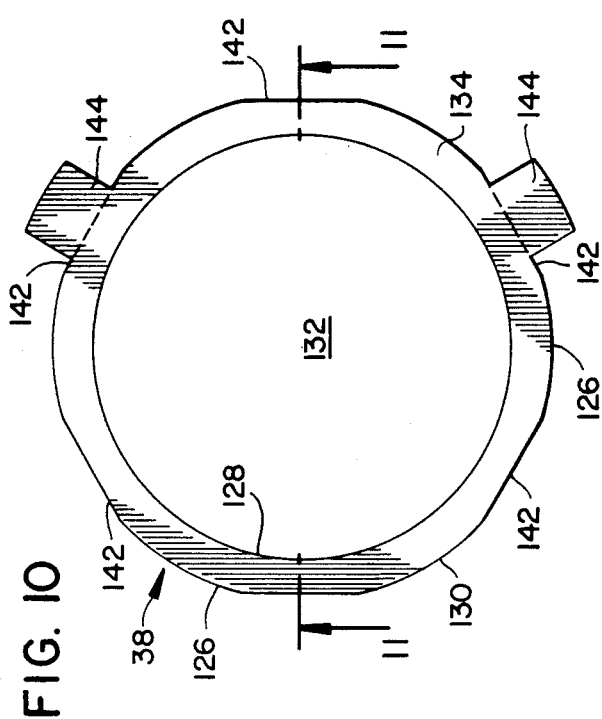
FIG. 10 is a top view of the second inner holder member of the positioning system shown in FIG. 1.
Figure 11:
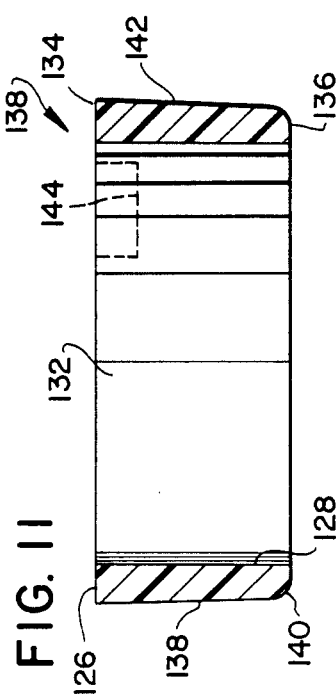
FIG. 11 is a view taken along line 11—11 of FIG. 10.

Next, a second sheet of transparent film 36 like first film 30 lies over interlocking member 34, well 20, and and sample 37. Last, another generally ring-shaped inner holder member 38, which is shown in detail in FIGS. 10 and 11, is ready to be force-fitted into inner holder member 32 along with second film 36, which will be gripped between inner locking member and the second inner holder member so that second film will be forced over sample 37 so as to sandwich sample 37 between the two films.

The above description of the mounting process shown in FIG. 1 is preceded by a process at the X-Ray spectroscopic machine that includes the following steps: (1) placing a master grid at the sample holder support plate at the spectroscope; (2) determining and recording the primary focus grid data relating to the position of the primary focus at the master grid; (3) translating the primary focus grid data at the master grid to assembly grid 26 and marking the position thereon. Sample 37 is placed onto first film 30 following the placement of interlocking member 34 into well 20 just prior to the positioning of second film 36 and after the stabilizing of outer and inner holders 28 and 32 in well 20. Sample 37 is placed into well 20 onto first film 30 at the mark (not shown) of the point of primary focus on assembly grid 26.

Before proceeding to a more detailed exposition of the sample holder assembly system shown in the embodiment of FIG. 1, a brief description of the elements shown in FIG. 1 shown in detail in FIGS. 2-11 will be made.

Grid support 24, shown in top and sectional side views in FIGS. 2 and 3, includes opposed top and bottom sides 40 and 42, respectively, with a circular recess 44 cut out of top side 40 to accommodate circular assembly grid 26. A key 46 extending downwardly from the circular outer surface 48 of the grid support is adapted to be received by a keyway 47 formed by assembly board 12 adjacent to well 20 so that when grid support 24 is positioned in well 20 it will be positioned in non-rotational relationship with the assembly board. Circular outer surface 48 of the grid support is adapted to be received in sliding relationship with circular inner surface of well 20. Four marks 50 around the rim of the grid support aid in aligning assembly grid 26 in recess 44.

Details of outer holder member 28, shown in FIGS. 4 and 5, include a circular wall 54 having an inner surface 56 and an outer surface 58 and having opposed top and bottom edges 60 and 62, respectively. Wall 54 defines a circular aperture 64 which is aligned with circular grid support 24 and particularly with circular assembly grid 26. Inner surface 56 includes a circular peripheral bead 66 spaced proximate to top edge 60. Inner surface 56 also forms an inwardly tapered surface 68 between bead 66 and bottom edge 62.

Inner holder member 32, shown in FIGS. 6 and 7, includes a circular wall 70 having an inner surface 72 and an outer surface 74 and having opposed top and bottom edges 76 and 78, respectively. Wall 70 defines a circular aperture 80, which is aligned with aperture 64 of outer member 28. Outer surface 74 forms a circular groove 82 spaced proximate to top edge 76 that is adapted to receive bead 66 of outer holder member 28 in snap-in relationship. Outer surface 74 forms an inward tapered surface 84 from groove 82 to bottom edge 78 so as to fit in gripping relationship with inner surface 56 of outer holder member 28. Outer surface 74 forms a circular inward chamfer 85 at bottom edge 78 so that when film 30 is mounted between outer and inner holder members 28 and 32 it will remain intact and not be torn when the film is stretched taut across the bottom face of inner holder member 32 as defined by bottom edge 78. Top edge 76 is spaced slightly above top edge 60 of outer holding member 28. A transverse, or radial, wide flange 86 extends outwardly from top edge 76 over top edge 60 of outer holder member 28. Flange 86 extends about 50 percent of the distance around top edge 76 over top edge 60, but this distance may vary. Flange 86 has opposed top and bottom sides 88 and 90, respectively, which extend beyond outer surface 74, with bottom side 88 being in pressing relationship with top edge 60 of outer holder member 28 when the outer and inner holder members are in their mounted position. A second, narrow flange 92 oriented diametrically opposite wide flange 86 also extends transversely, or radially, outwardly from top edge 76 also over top edge 60 of outer holder member 28; narrow flange 92 has opposed top and bottom sides 94 and 96, respectively, with bottom side 96 being in pressing relationship with top edge 60 of outer holder member 28 when the outer and inner holder members are in the mounted relationship. An aligning mark 98 shown on top side 94 of narrow flange 92 is for aligning the assembled sample holder when it has been removed from well 20 and the sample holder is being aligned with a mating mark at the sample holder support plate at the spectrometer.

Interlocking member 34, shown in detail in FIGS. 8 and 9, includes a circular upright wall 100 having opposed inner and outer surfaces 102 and 104, respectively, forming a circular aperture 106 aligned with apertures 64 and 80. Wall 100 includes top and bottom edges 108 and 110, respectively. Outer surface 104 is adapted to be slidingly received and mounted by inner surface 21 of well 20. Bottom edge 110 includes a dropped narrow outward bottom edge portion 112 that is adapted to be in contact with a mating portion of top edge 60 of outer holder member 28 that lies free of coverage by wide flange 86 and another raised broad bottom edge portion 114 that is adapted to be in contact with both top edge 76 and with top side 88 of wide flange 88 of inner holder member 32. A key 116 extending downwardly from outer surface 104 at a position diametrically opposite the center of the arc of bottom edge portion 114 is adapted to be received by keyway 47 at well 20 so that interlocking member 34 is retained in non-rotational relationship with assembly board 12. A space 118 formed in bottom edge portion 112 adjacent to key 116 is adapted to receive narrow flange 92 of inner holder member 32. Interlocking member 34 engages, or aligns, inner holder member 32 in non-rotational relationship with itself and with assembly board 12, and thus with grid support 24 and assembly 26, as follows. Wide flange 86 forms a pair of transverse steps 122 at the ends of the arc of wide flange 86; and the bottom edge portions 112 and 114 form a pair of vertical steps 124 adapted to lock with steps 122 so that inner holding member 32, along with snap-locked outer holder member 28, is prevented from any rotation in well 20. It is noted that narrow flange 92 positioned in space 118 also is adapted to prevent rotation of inner holder member 32.

The other, or most inner, inner holder member 38, which is shown in detail in FIGS. 10 and 11, includes a circular upright wall 126 having inner and outer surfaces 128 and 130, respectively, and having opposed top and bottom edges 134 and 136, respectively. Wall 126 forms a circular aperture 132, which is aligned with apertures 64, 80, and 106 of outer holder member 28, inner holder member 32, and interlocking member 34. Bottom edge 136 defines a bottom face that is aligned with the bottom faces of outer and inner holder members 28 and 32. Outer surface 130 forms an inward taper between top and bottom edges 134 and 136; outer surface 130 is adapted to press fit against straight inner surface 72 of inner holder member 32 so that other inner holder member 38 is held in non-rotational and locked relationship with inner holder member 32. As inner holder member 38 is press-fitted into inner holder member 32, second film 36 is pressed into gripping relationship between inner surface 72 and outer surface 130, and in the final mounted position second film 36 forms a taut surface across the bottom face at bottom edge 78. Second film 36 sandwiches sample 37 with the first film 30 in the final mounted position. An inward chamfer 140 is formed at the intersection of outer surface 130 and bottom edge 136 so the second film 36 remains intact during and after the mounting process and does not tear.

A series of vertical cutouts 142 are formed in outer surface 130 of inner holder member 38 so that air passages are formed between outer surface 130 and inner surface 72 of inner holder member 32 so that trapped air between first and second films 30 and 36 is allowed to escape to the atmosphere; thus, first and second films 30 and 36 are retained in their taut mode so that wrinkling does not occur. Cutouts 142 terminate at a distance from bottom edge 136 because of taper 138.

A pair of transversely spaced flanges 144 extending from top edge 134 are adapted to be passed through a pair of recesses 146 formed at inner surface 102 at top edge 108 of interlocking member 34. Flanges 144 act as stop members when inner holder member 38 is fully mounted with inner holder member 32.

Figure 1A:
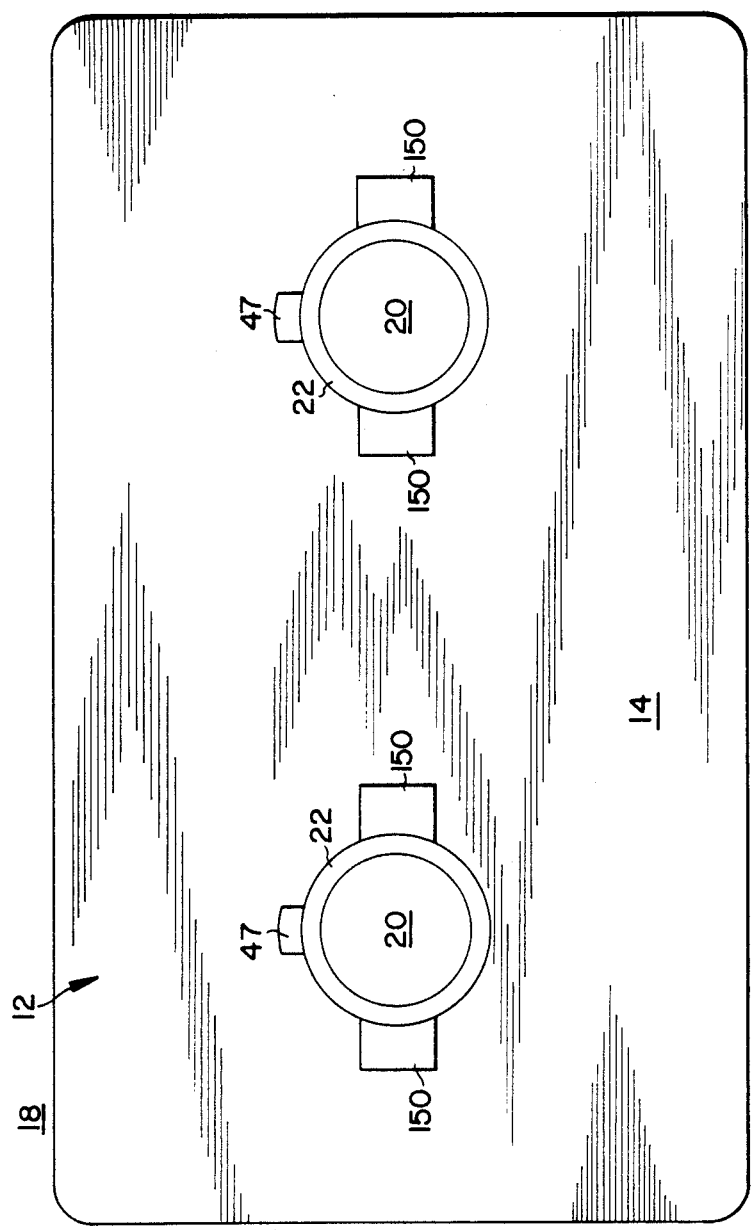
FIG. 1A is a plan view of the assembly board and well.

FIGS. 1 and 1A show assembly board 12 including keyway 47 and circular step 22 extending into well 20. A pair of opposed recesses 150 in top surface 14 opening to well 20 allows an operator to grip the elements assembled in the well.

Figure 12:
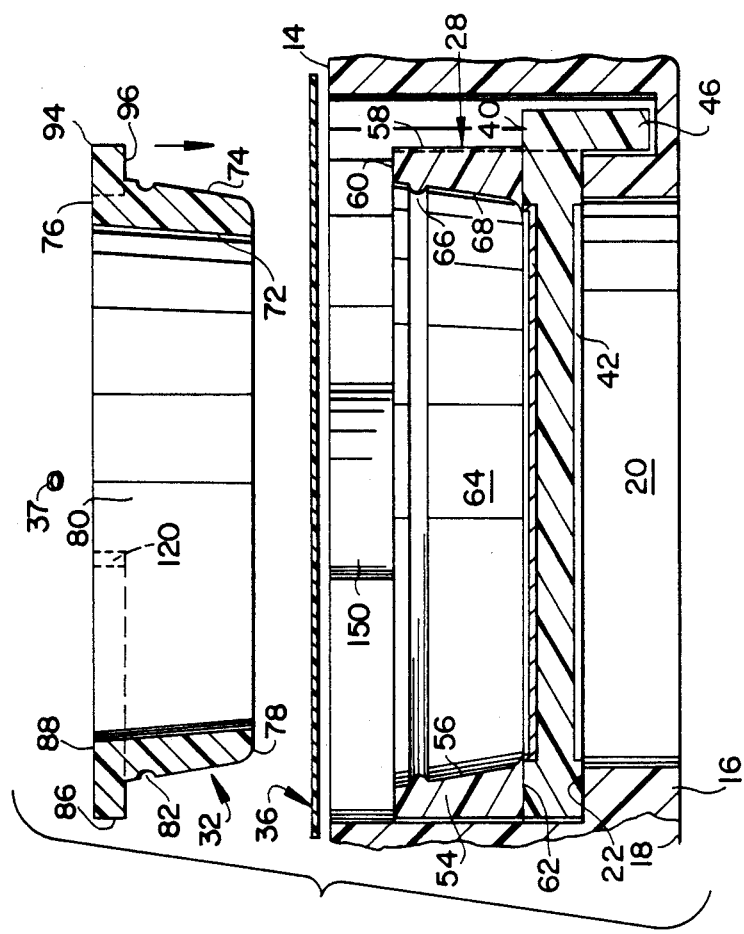
FIG. 12 is a side view of the assembly system being assembled.

System 10 is shown in the process of being assembled in well 20 in FIGS. 12, 13, and 14. Grid holder 24 has been set upon seat 22, outer holder member 28 has been set upon the rim of top surface 14 of grid holder 24, inner sample holder 32 has been snap-fitted into outer holder member 28 with first film 30 gripped between the two holders and stretched taut across the bottom face of inner holder member 32 with sample 37 positioned upon first film 30. It is particularly to be noted that sample 37 is placed upon first film 30 over the mark on assembly grid 26 that aligns the sample with the primary focus of the X-Ray only after interlocking member 34 has been positioned into locking relationship with inner holder member 32 so that there will be no rotation of first film 30 afterwards that would remove sample 37 from the focus point. Interlocking member 34 has been keyed into well 20 with vertical steps 120 locked with transverse steps 122 of inner holder member 32 so as to hold inner holder member 32 and outer holder member 28 in non-rotational relationship with grid support 24 and particularly with assembly grid 26. Second sheet of film 36 is shown ready for descent into well 20 with the last inner holder member 38 shown in a descending mode about to press second film 36 into inner holder member 32 over first film 30 and sample 37. Air 141 trapped between films 30 and 36 will be forced out of the well area by way of air passages 142.

Figure 15:
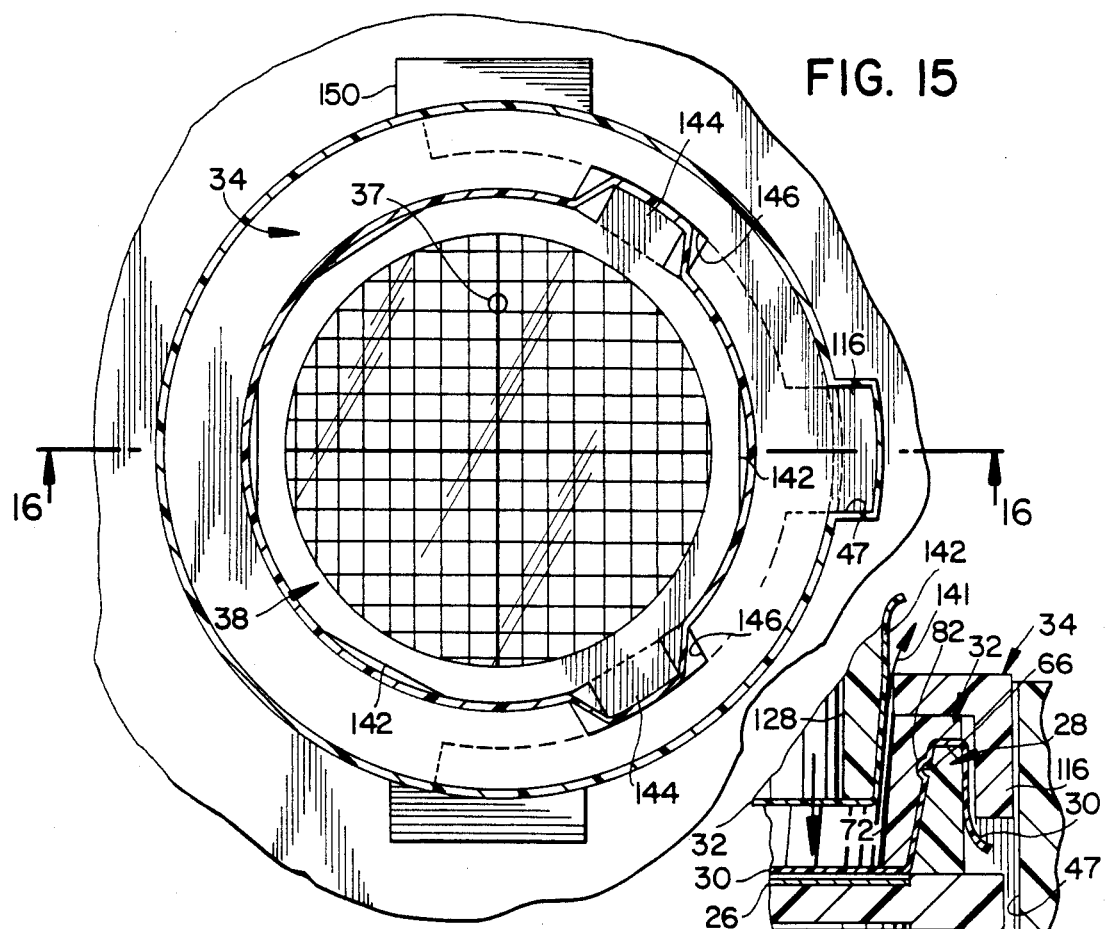
FIG. 15 is a top view of an assembled two-film system.
Figures 16, 17:
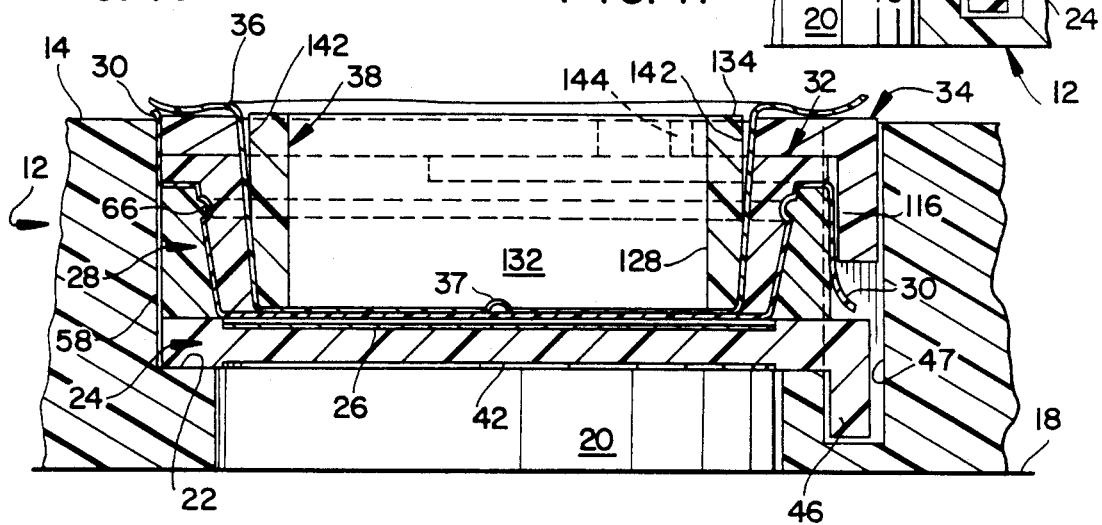
FIG. 16 is a sectional view taken through line 16—16 of FIG. 15.
FIG. 17 is a detailed view of FIG. 16 showing the air passage.

FIGS. 15 and 16 illustrate system 10 in a fully assembled mode with grid support 24, outer holder member 28, inner holder member 32 interlocking member 38, and first film 30 being in the same positions as shown in FIG. 15. Here, however, inner holder member 38 is now positioned in well 20 and press-fitted with inner holder member 32 with second film 36 gripped between them and pulled tautly into sandwiching relationship with sample 37 and first film 30. The most outer portions of inner holder member 38 are adapted to pass through aperture 106 with stop flanges 144 passing through recesses 146 of interlocking member 34.

FIG. 17 illustrates the escape of air 141 from between film sheets 30 and 36 through cutouts 142 that form air passages between inner surface 72 of inner holder member 32 and outer surface 130 of the other inner holder member 38.

Figure 18:
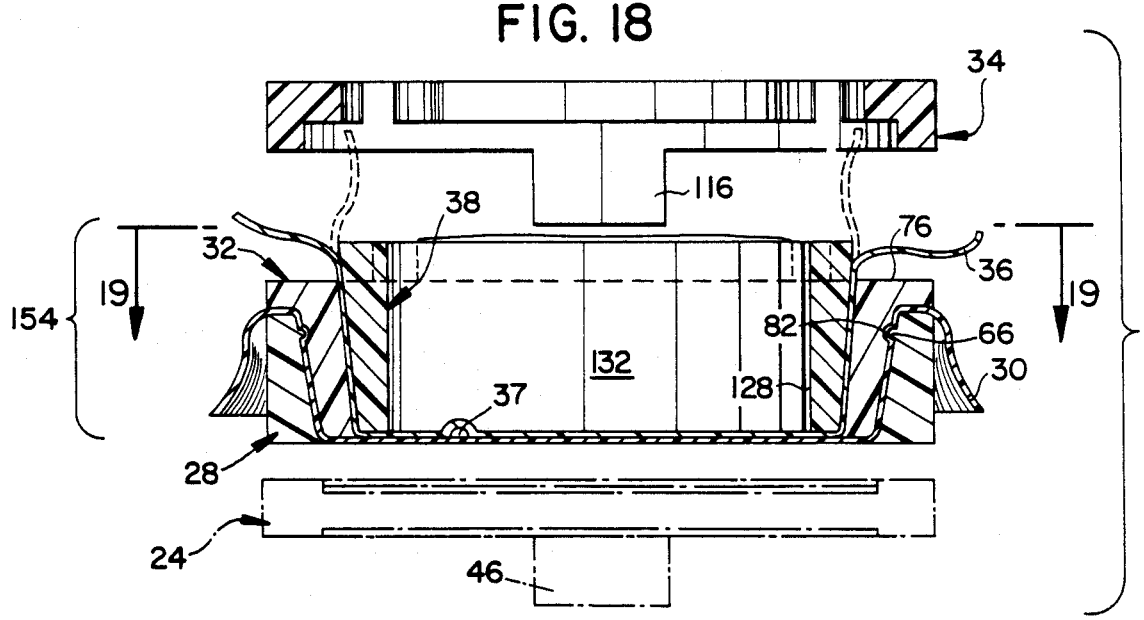
FIG. 18 is a sectional side view of the system according to the present invention after assembly and in the process of being removed from an assembly board.
Figure 19:
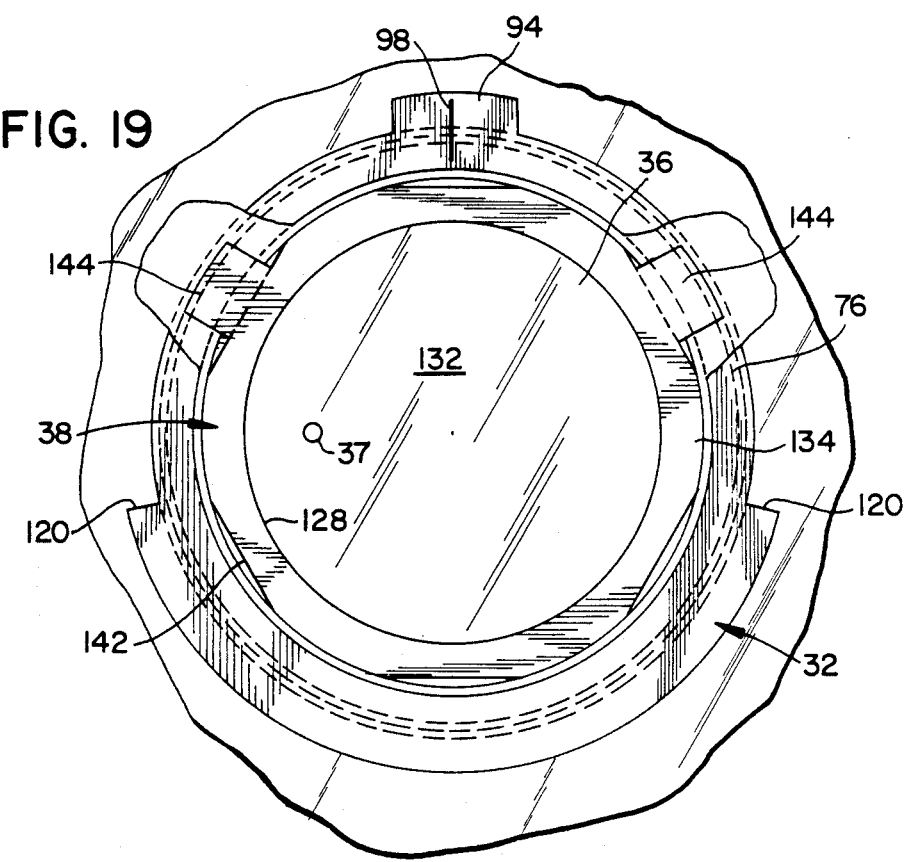
FIG. 19 is a view taken through line 19—19 of FIG. 18.

FIGS. 18 and 19 illustrate system 10 after assembly in the process of being removed from assembly board 12, which is not illustrated for purposes of clarity. Here outer holder member 28, inner holder member 32, and the most inner holder member 38 are in locked relationship to form an assembled sample holder 154, which includes first and second films 30 and 36 sandwiching sample 37. The first step after assembly of system 10 is the removal of interlocking member 34 from well 20 and out of locking relationship with inner holder members 32 and 38. Then assembled sample holder 154 is removed form well 20 and from grid support 24. Sample holder 154 is then transported to the spectrometer and placed into the sample holder support plate there with mark 98 on inner holder member 32 aligned with an aligning mark at the support plate so that sample 37 is aligned with the point of primary focus.

Figure 20:
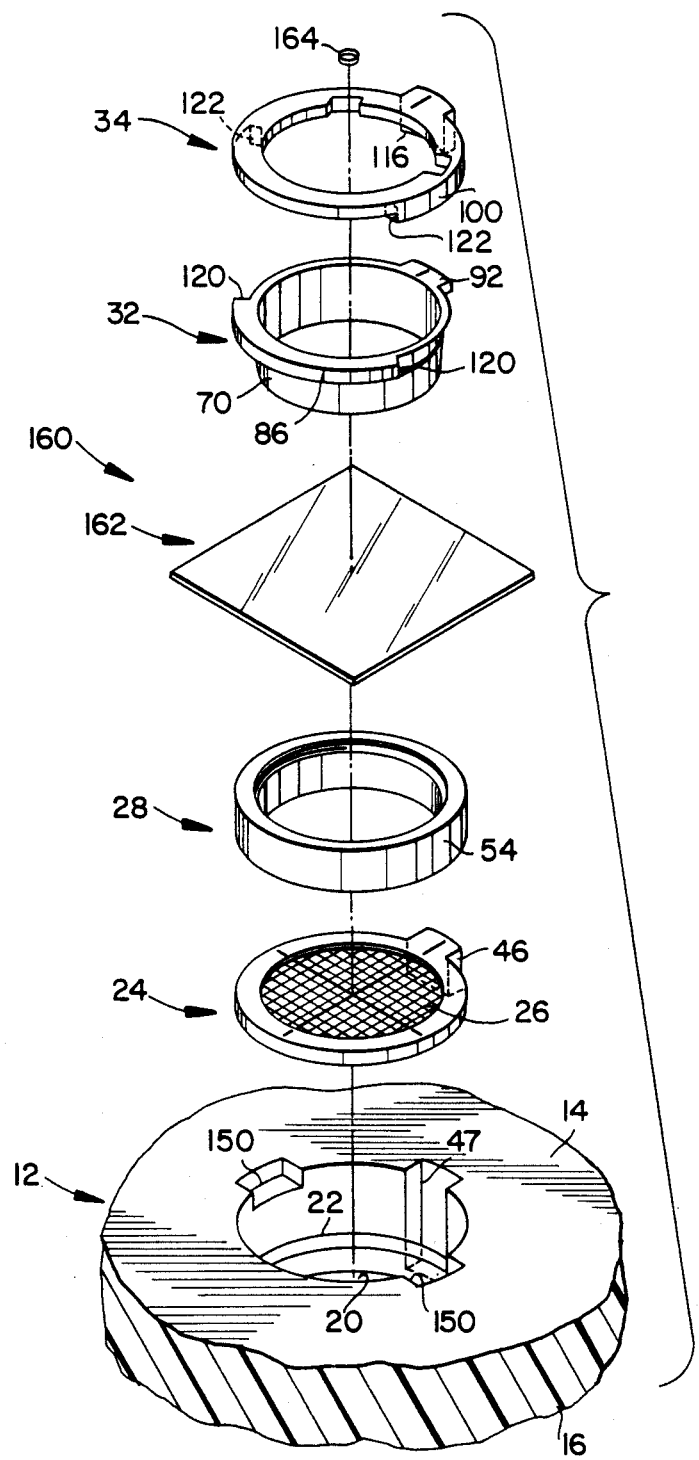
FIG. 20 is an exploded-type perspective view of a sample positioning system for one layer of film.

Another embodiment of the present invention is shown in FIG. 20 where a single film sample holder assembly system 160 is shown in exploded perspective view. The steps of assembly and the elements are the same as that shown and described in FIGS. 1-19 with the exception of second sheet of film 36 and inner holder member 38. In particular, grid support 24 with assembly grid 26 is first positioned in well 20 upon circular step support 22, then outer holder member 28 is placed in well 20 upon the rim of grid support 24, then a single sheet of film 162 is placed over well 20, then inner holder member 32 is placed into well 20 and into outer holder member 28 at the same time forcing film 164 into gripping relationship between the walls of inner and outer holder members 28 and 32 and stretched taut across the bottom face of inner holder member 32. Interlocking member 34 is then locked into well 20 by positioning key 116 into keyway 47 and further locked to flanges 86 and 92 of inner holder member 32. Last, a sample 164 is positioned on film 162 over the mark made on assembly grid 26 in accordance with the grid data determined relative to the primary focus of the X-Ray beam at the master grid at the spectrometer.

Figure 21:
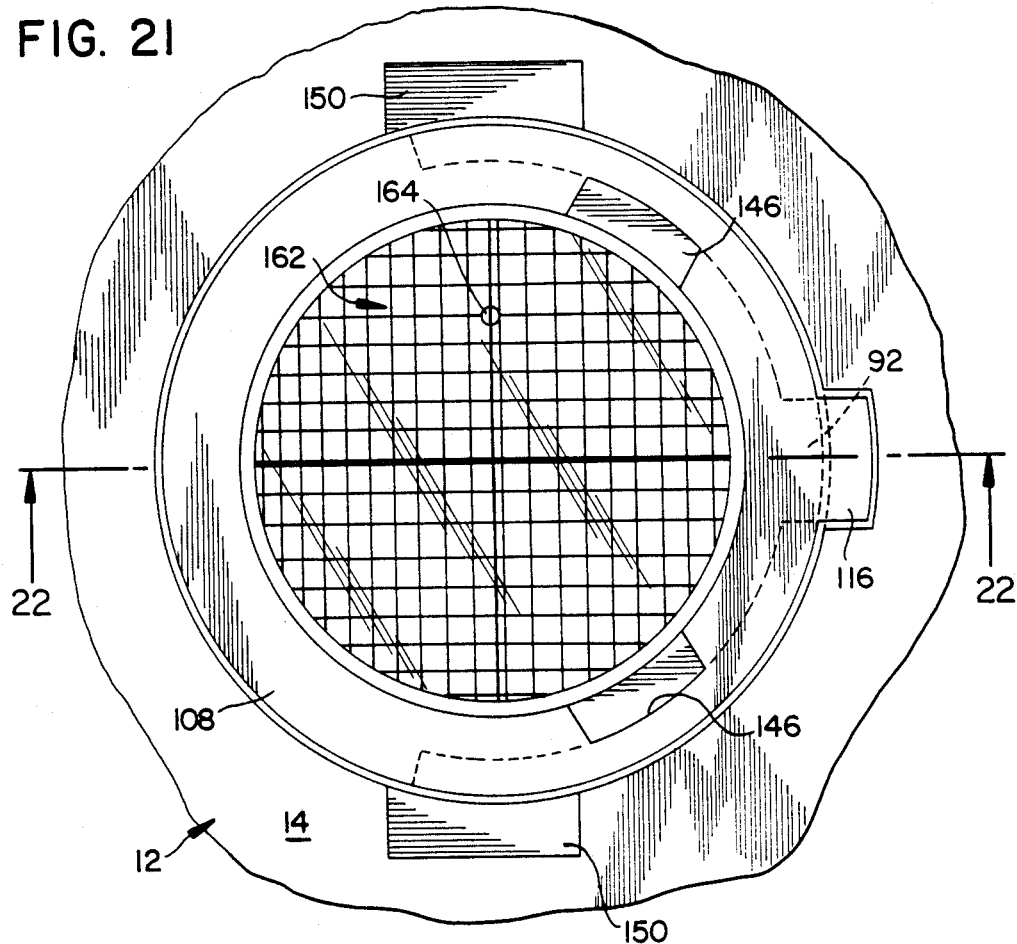
FIG. 21 is a top view of the assembled system shown in FIG. 20.
Figure 22:
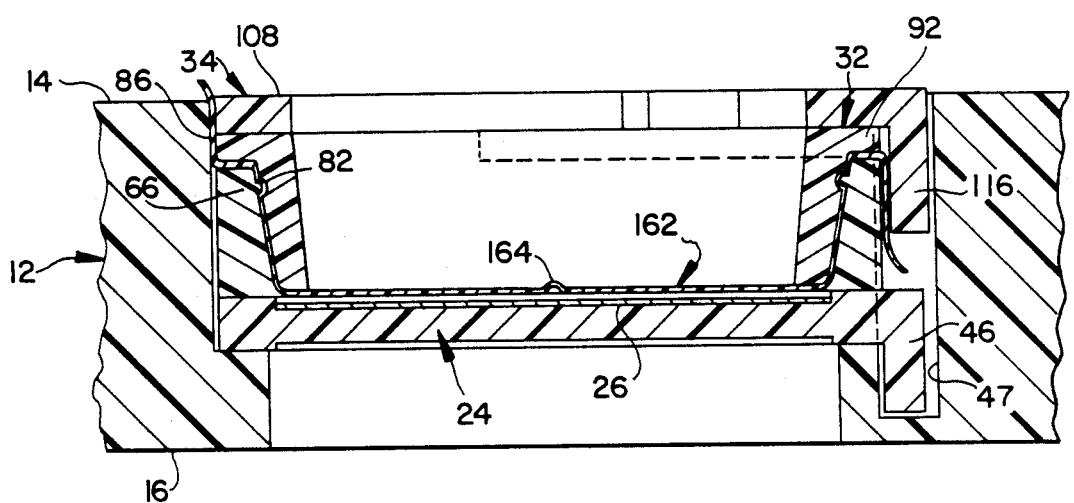
FIG. 22 is a view taken through line 22—22 of FIG. 21.

FIGS. 20 and 21 show system 160 in the assembled mode in well 20 with grid support 24 on step 22, outer holder member 28 resting on the rim of grid support 24, inner holding member 32 snapped into outer holder member 28 with film 162 griped between the outer and inner holder members, sample 164 positioned on film 162 over the marked point of primary focus, and interlocking member 34 keyed to assembly board 12 and locked to the top edge of inner holder member 32 at flanges 86 and 92.

Figure 23:
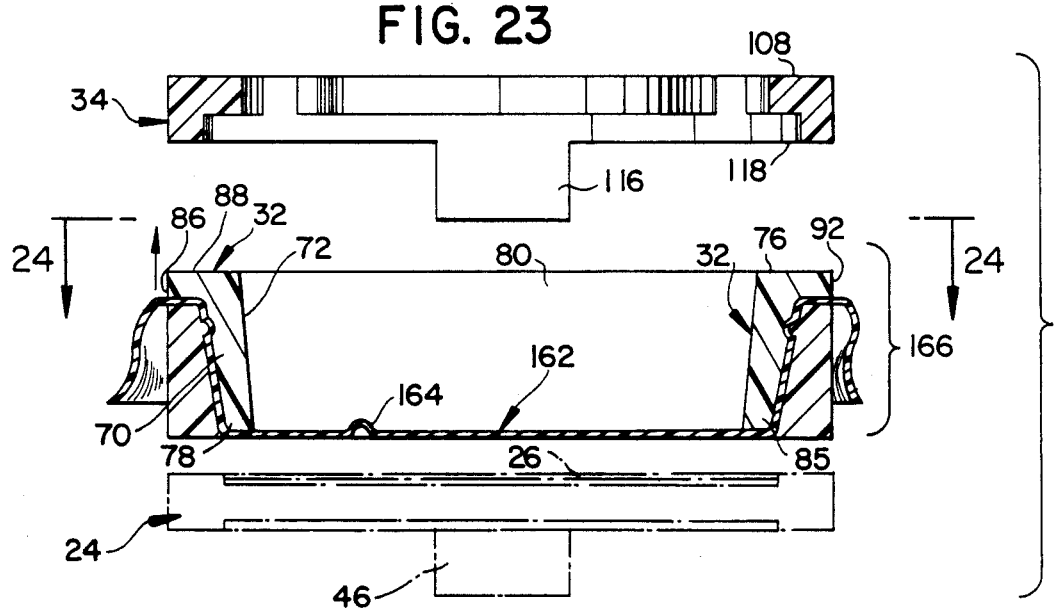
FIG. 23 is a sectional view of the sample positioning system shown in FIG. 24 with the interlocking member being removed from the sample holder and the sample holder being removed from the grid support.
Figure 24:
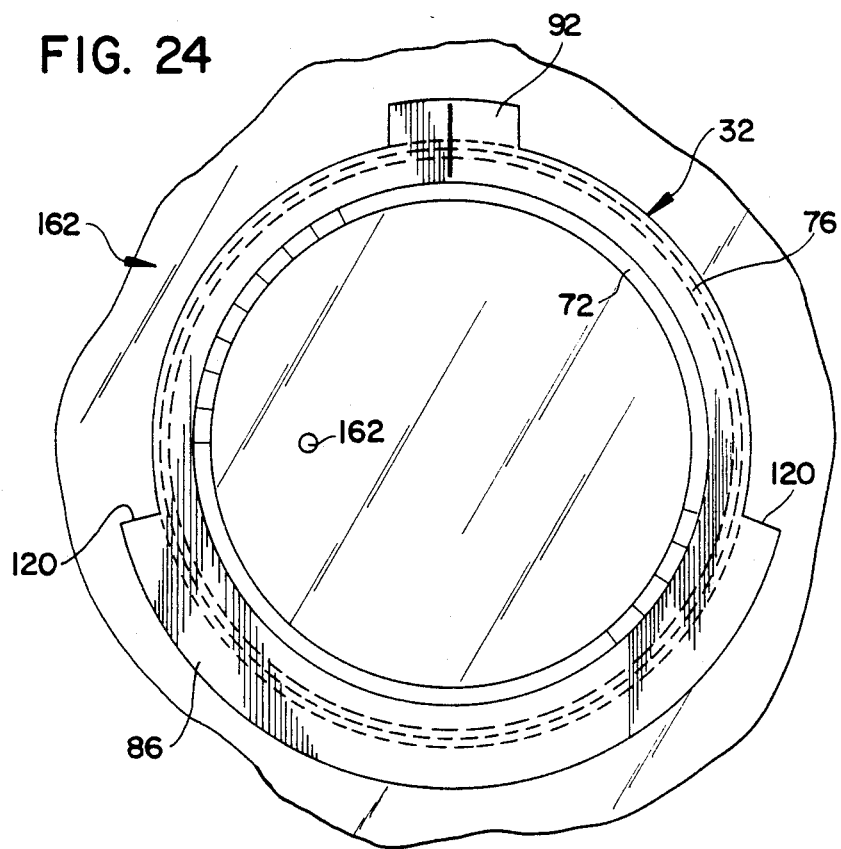
FIG. 24 is a top view taken through line 24—24 of FIG. 23.

In FIGS. 23 and 24 assembly system 160 is in the process of disassembly from assembly board 12 (not shown) with interlocking member 34 having been raised from the well. Outer and inner locking members 28 and 32 in their locked mode now designated sample holder 166 are being moved from the well with film 162 and sample 164 for subsequent transportation to the spectrometer for positioning at the sample holder support plate where sample 164 will automatically assume its position at the point of primary focus.

Another embodiment of the present invention is shown in FIG. 25 in an exploded perspective view as system 170. A generally cylindrical grid support 172, shown in plan detail in FIG. 26, is shown resting upon a support surface 174 such as a table with an assembly board 176 having a vertical circular well 178 descending upon grid support 172 for positioning in well 178. An interlocking member 180, shown in isolation in FIGS. 27 and 28, is shown ready for descent into well 178 with an inner holder member 182, shown in isolation in FIGS. 29 and 30, also ready for positioning in well 178. A first sheet of film 184 is shown over inner holder member 182 with a sample for analysis positioned over first sheet followed by a second sheet of film 188. An outer holder member 190 is finally shown over second film 188 ready for pressing first and second films 184 and 188 into inner holder member 182 in well 178. Sample 186 is positioned against an assembly grid 192 positioned at the top of grid support 172 over a mark upon the assembly grid that is in accordance with grid data transferred from the master grid at the spectroscopic machine that marks the point of primary focus of the X-Ray beam.

Grid support 172 includes a generally cylindrical member having a main cylindrical portion 194, a bottom cylindrical portion, and a top cylindrical portion, with the main cylindrical portion having a main diameter, the top portion having a top diameter, and the bottom portion having a bottom diameter, the bottom diameter being greater than the main diameter, and the main diameter being greater than the top diameter. Assembly grid 192 is positioned at the top surface of top cylindrical portion, and the bottom surface of bottom cylindrical member rests upon support surface 174.

As is also seen in FIGS. 24, 25, and 29, assembly board 176 has opposed top and bottom surfaces 200 and 202, respectively, and includes a circular support flange 204 that is positioned between top and bottom surfaces 200 and 202 and that extends into well 178. Well 178 extends between top and bottom surfaces 200 and 202 and includes a top portion, a middle portion formed by flange 204 that is adapted to receive main cylindrical portion of the grid support, and a bottom portion that is adapted to receive bottom cylindrical portion 196 of the grid support. Assembly board forms a vertical keyway 206 adjoining both well 178 and support flange 204 that opens upwardly at top surface 200 of the assembly board. A downwardly extending key 208 extending from the bottom of support flange 204 is adapted to be received by a keyway 210 in bottom cylindrical portion 196 of grid support 172. Thus, when grid support is positioned in well 178, grid support 172 is locked in non-rotational alignment with assembly board 176.

Interlocking member 180, which is shown in detail in FIGS. 27 and 28, is analogous to interlocking member 34 of assembly systems 10 and 160 described previously. Interlocking member 180 includes a circular wall 212 having inner and outer surfaces 214 and 216, respectively, and top and bottom edges 218 and 220, respectively, and forming a central aperture 222 adapted to fit over circular assembly grid 192. A key 224 depending from outer surface 216 is adapted to be received by keyway 206. Bottom edge 220 is flat and is adapted to rest upon support flange 204. Interlocking member 180 differs in construction from interlocking member 34 of systems 10 and 160 in that the locking side is reversed from the prior described member; that is, in system 170 being described, the locking side faces upwardly opposite from key 224, as will be described, while in the prior system, the locking side faced downwardly. In particular, a top edge 218 includes a first portion 226 that extends entirely around wall 212 and a second portion 228 that is raised from top edge 218 and extends about halfway around the outer half of top edge 218 from either side of key 224. A space 230 is formed by two halves of second portion 228 positioned at key 224.

Inner holder member 182 is identical to inner holder member 34 described previously in relation to system 10, except that it is reversed in its direction of descent from that described in system 10 so that it may engage with first and second portions 226 to 228. In particular, inner holder member includes a circular wall 232 having a vertical inner surface and a top to bottom outwardly tapering outer surface and top and bottom edges with a circular groove extending around the lower part of the outer surface. A radial, or transverse, wide flange 234 extends outwardly from the bottom edge of wall 232. A second narrow flange 236 also extends transversely outwardly from wall 232 diametrically opposite wide flange 234. Wide flange 234 is adapted to be positioned at first portion 226 of interlocking member 180 and narrow flange 236 is adapted to be positioned in space 230 at second portion 228. Thus, when inner holder member 182 is set upon interlocking member the two members engage in a non-rotational relationship with one another.

Outer holder member 190 is identical to outer holder member 28 discussed previously with reference to system 10 except that it is reversed in its direction of descent into the well. Outer holder member 190 includes a circular wall 238 having inner and outer surfaces and top and bottom edges with the inner surface tapering from the bottom edge to the top edge. A circular bead extends around the bottom area of the inner surface that is adapted to snap-fit into the circular groove of inner holder member 182.

Figure 31:
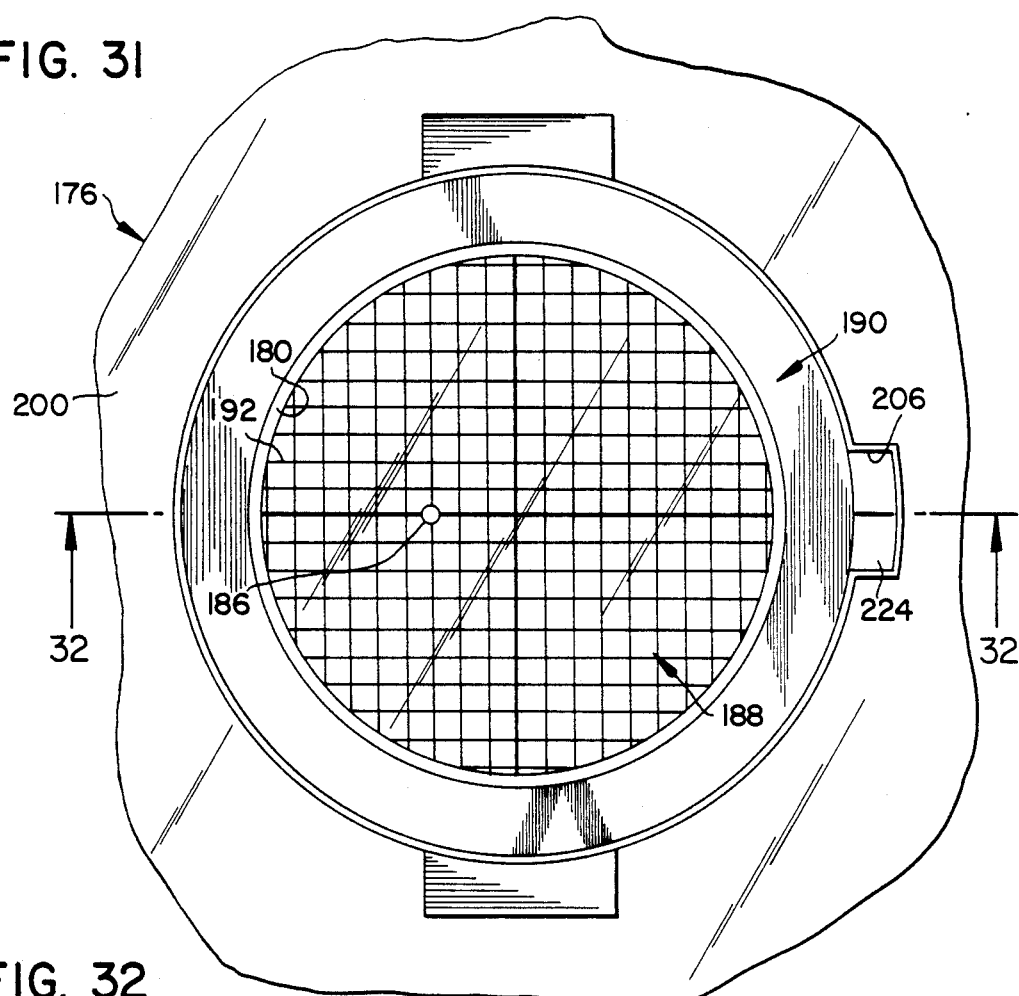
FIG. 31 is top view of the assembled system shown in FIG. 25.
Figure 32:
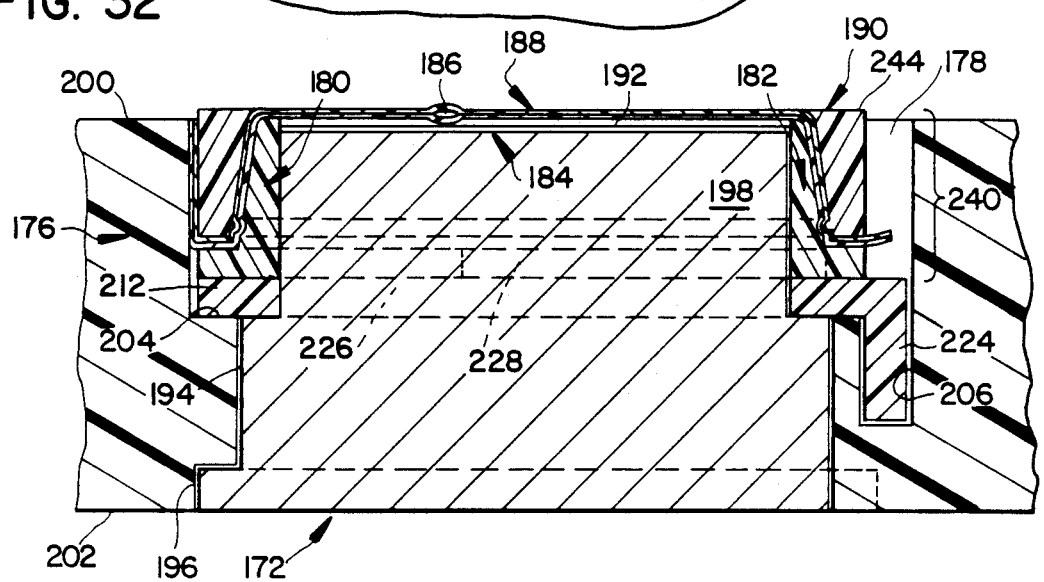
FIG. 32 is a sectional view taken through line 32—32 of FIG. 31.

System 170 is shown in its assembled mode in FIGS. 31 and 32 where inner and outer holder members 184 and 190 now together comprise sample holder 240 carrying first and second films 184 and 188 sandwiching sample 186. Sample holder 240 will subsequently be separated from interlocking member 180 after being separated from grid support and removed from well 178.

Assembly grid 192 is positioned slightly below the level of top surface 200 of assembly board 176. The top edges of inner and outer holder members 184 and 190, on the other hand, are at about the same level at top surface 200. When outer holder member 190 is press fitted onto inner holder member 182, first film 184 is stretched tautly across the top face of the aperture formed by the top edge of inner holder member 182 directly over assembly grid 192.

Sample 186 is positioned over first film 184 after film 184 is laid across well 178 over inner holder member 182, and only when the sample is aligned to the grid mark indicating the point of primary focus of the X-Ray beam is second film 188 laid over first film 184 and outer holder member 190 pressed onto inner holder member 182.

System 170 can be adapted to a single sheet of film as follows. After a single sheet of film 184 is laid over well 178, assembly grid 192, and inner holder member 182, outer holder member 190 is press fitted onto the inner holder member with film 184 stretched tautly across the top face of inner holder member 182. At his time a sampe (not shown) can either be affixed to film 184, for example by gluing, or, in the case of a liquid sample, by wetting the face of the film, in either case at the data point of the primary focus of the beam.

Figure 33:
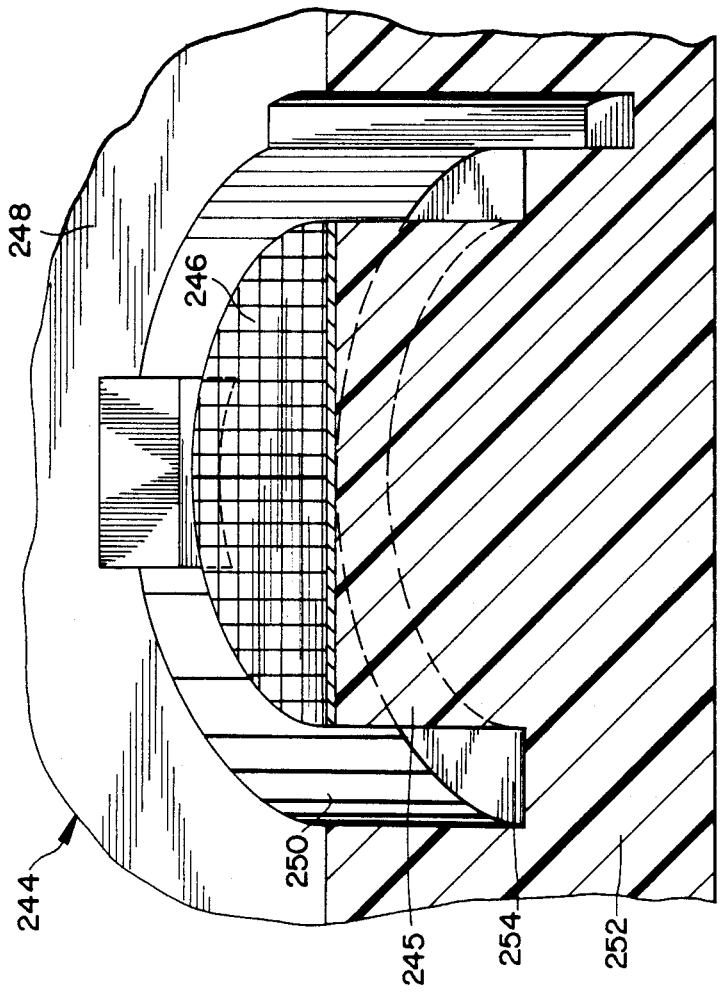
FIG. 33 is a perspective of a unitary assembly board and grid support analogous to those elements as shown in FIG. 25.

FIG. 33 illustrates in sectioned perspective view a unitary assembly board and grid support member 244 for a sample holder assembly similar to the system shown in FIG. 25. An assembly grid 246 located at the top of grid support 244 is aligned with the top surface 248. A circular well 250 separates grid support 244 and assembly board body 252. A circular support surface 254 is adapted to give a bearing support for interlocking member 180. A vertical slot, or keyway, 256 adjoining circular well 250 is adapted to accept key 224 of interlocking member 180. A pickup recess 258 for convenient removal of the assembled sample holder from well 250 into which inner and outer holder members 182 and 190 are mounted during assembly is formed at the top surface of unitary member 244.

Figure 34:
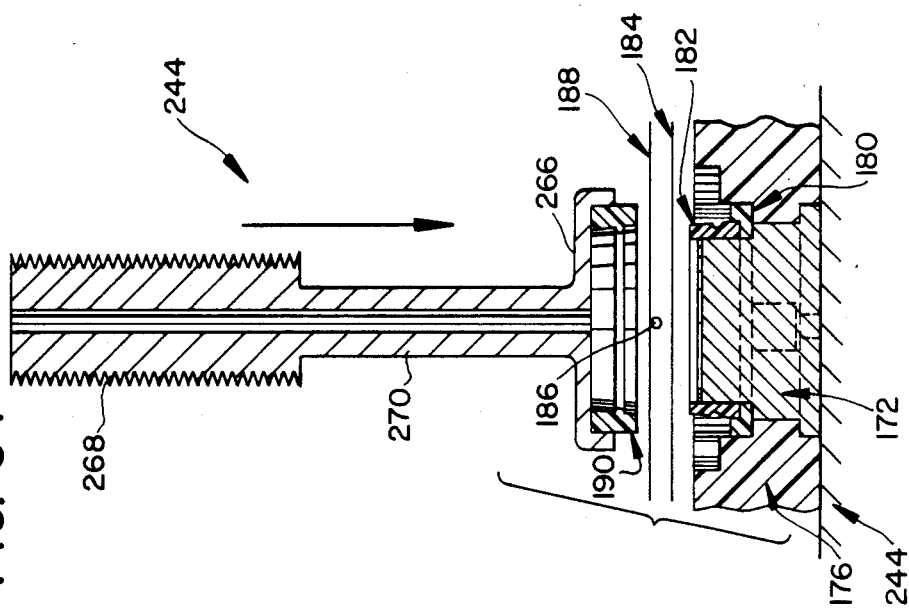
FIG. 34 is a sectional view of a mounting tool used to assemble an outer holder member to an inner holder member in the assembly system of FIGS. 25 and 33.

A mounting tool 244 for forcing outer holding member 190 into snap-in relationship with inner holder member set into circular well 250 of a unitary mounting member 244 is illustrated in FIG. 34. A circular, recessed bottom gripper 266 holds ringed inner holder member 182 in position ready for press mounting into well 250. The operator holds tool 244 at a handle 268 that is positioned at the end of stem 270 opposite gripper 266.

Figure 35:
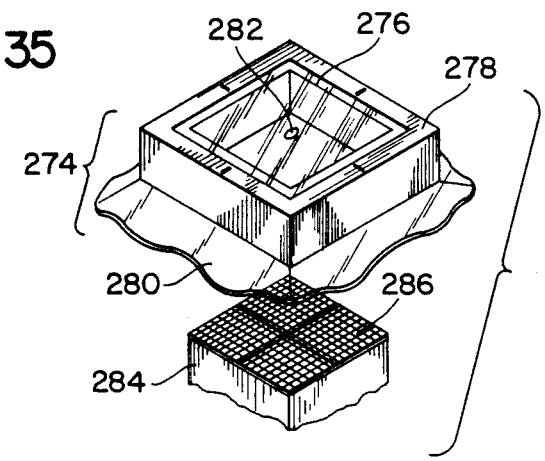
FIG. 35 is a perspective view of an sample positioning system having a square configuration.

FIG. 35 shows an alternative assembly system 272 to the circular and ring-shaped configurations shown for the well and assembly elements discussed previously. A square-shaped sample holder 274 comprising square inner and outer holder members 276 and 278, respectively, snap-locked together with a film 280 gripped between them with a sample 282 positioned on the film is shown being raised from a square grid support 284 with a top assembly grid 286, which has been marked with the data for the point of primary focus with which sample 282 has been aligned. System 272 has the advantage of dispensing with the keyed elements of the systems described previously.

Figure 36:
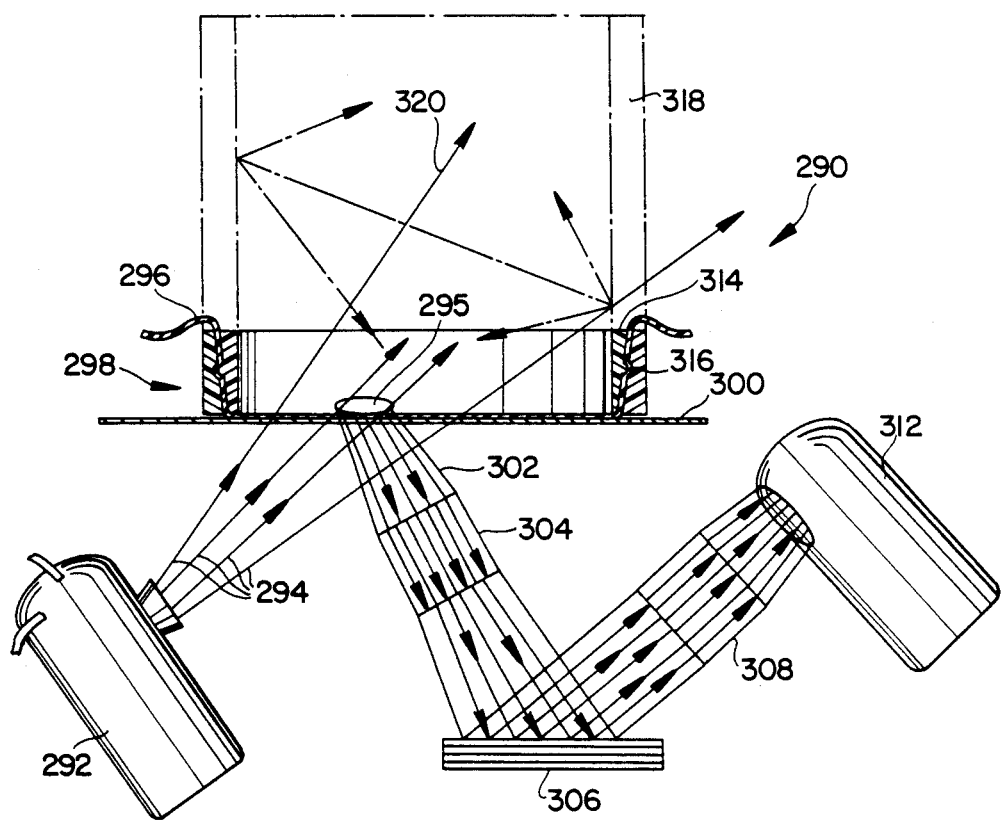
FIG. 36 is a schematic representation of an inverted-optics spectroscope holding a sample holder of the types shown in the embodiments of FIGS. 1 and 20.

FIG. 36 illustrates an inverted optics spectroscope 290 that includes an X-Ray source tube 292 that generates X-Ray beams 294 directed at a sample 295 that lies upon a sheet of film 296 supported by a sample holder 298 that is in turn supported by supporting plate 300 that has an aperture at its center to pass X-Ray beams 294 to sample 295. X-Ray beams 302 are reflected from sample 295 to a collimator 304 from where the reflected beams are directed to analyzer crystal 306, from where the beams are directed to another collimator 308 and then to detector 312. In the present invention, sample holder 298 comprises low profile inner and outer holder members 314 and 316, respectively, which grip film 296 so that beams 294 that pass around sample 295 pass over the low profile walls of sample holder 298. Prior art high profile sample holder 318 is shown in phantom line with reflected X-Ray beams 320, also shown phantom line, bouncing from the high profile walls of prior art sample holder 318 with a resulting creating or static, or noise, that interferes with the analysis of sample 295.

Figure 37:
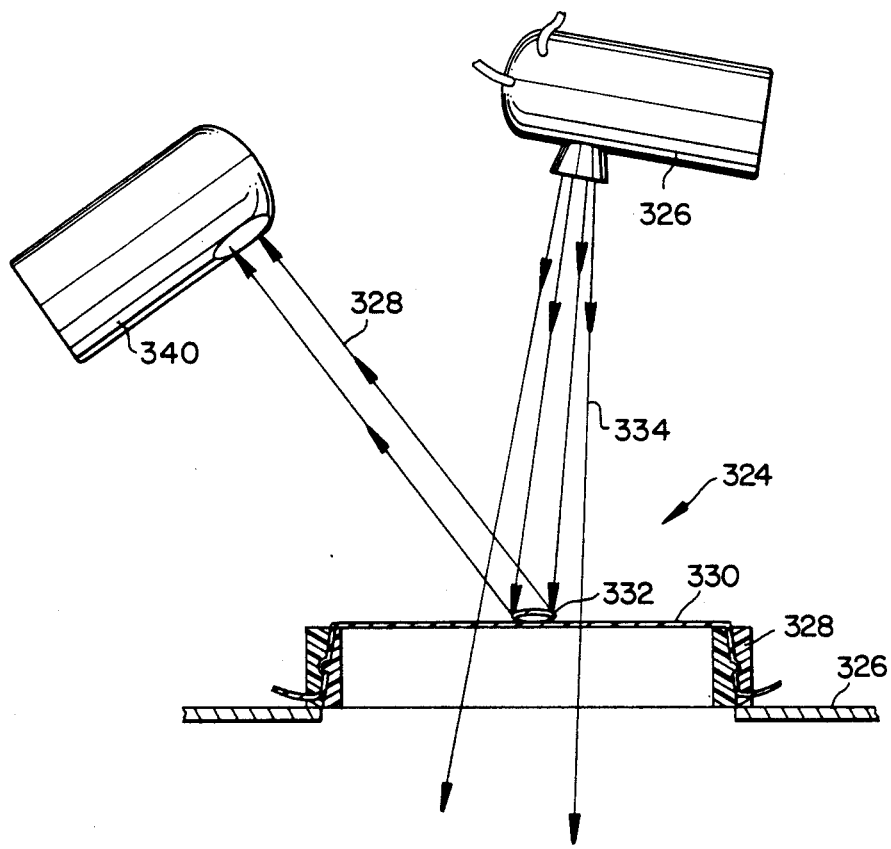
FIG. 37 is a schematic representation of a vertical optics spectroscope holding a sample holder of the type shown in FIG. 25.
Figure 38:
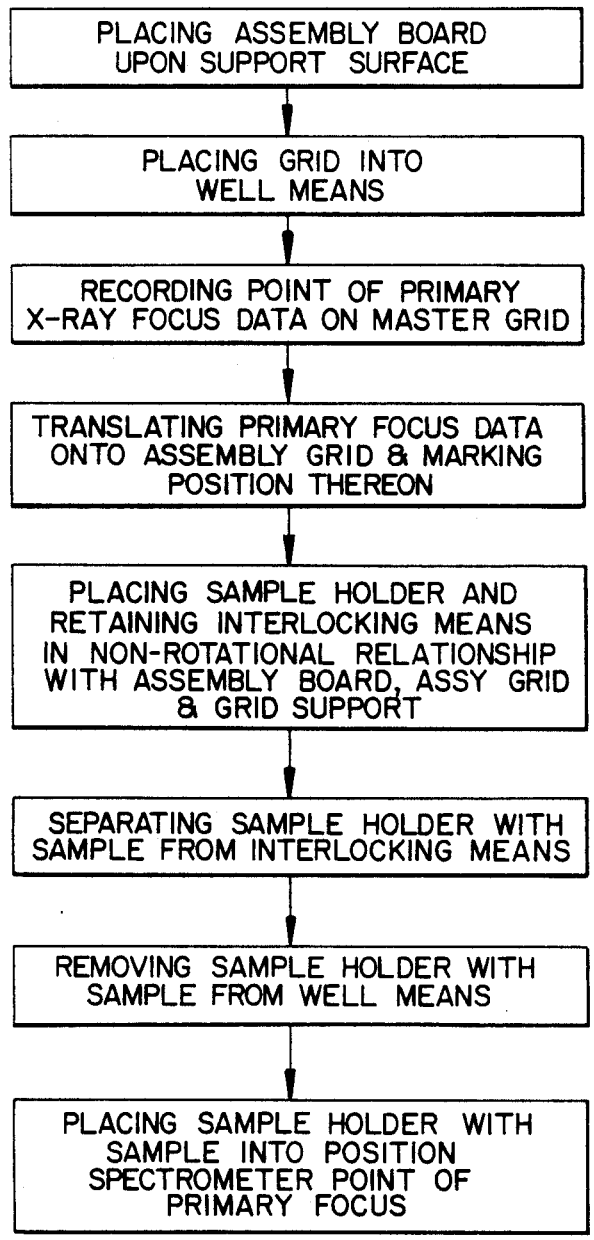
FIG. 38 is flow block diagram illustrating the steps of claim 1.

FIG. 37 illustrates a vertical optics spectroscope 324 that is adapted to mount the sample holder shown in the embodiment of FIG. 20. Here, a supporting plate 326 holds a sample holder 328 supporting a single sheet of film 330 upon which is mounted a sample 332 which is directly exposed to an X-Ray beam 334 directed from an X-Ray tube 336. Sample 332 has previously been mounted at the prime focus of the beam. Reflected beams 338 from sample 332 are received at X-Ray detector 340.

The film sheets or layers described hereinabove can be ordinary film of a thickness known in the art, or they can be thins films. Thin films as a term used in this application are films in the approximate thickness of 1 to several micrometers in thickness. The term micro-sample as used herein as a sample of small size. The term mini-sample as used herein is a sample in the approximate range of 0.01 micrometers to several millimeters. These terms are relative and are not to be considered as restrictive and are meant to be illustrative.

It is to be understood that the foregoing embodiments of the invention are only illustrative and that modifications thereof may occur to those skilled in the art. Accordingly, this invention is not to be regarded as limited to the embodiments disclosed herein, but is to be limited only as defined in accordance with the appended claims.

What is claimed is:

1. A method of positioning a sample for X-Ray spectroscopic analysis at a spectroscopic machine having an X-Ray beam, comprising the following steps:
   (a) placing an assembly board having opposed top and bottom surfaces with the bottom surface upon a support surface, the board having a generally upright well means having an inner surface;
   (b) placing a grid support having an outer surface adapted to be sliding received by the inner surface of the well means into the well means, which is for receiving the grid support, the grid support having a top side and an upwardly facing assembly grid, the grid support and the assembly board including keying means for retaining the grid support in non-rotatable relationship with the assembly board and support means extending into the well means;
   (c) recording the point of primary focus data of said X-Ray beam onto a master grid; said X-Ray beam onto a master grid;
   (d) trasladintg the primary focus grid data at the master grid onto the assembly grid and marking the position thereon;
   (e) placing sample holder and interlocking means for retaining the sample holder in non-rotational relationship with the assembly board and with the grid support and assembly grid mounting at least one sheet of transparent film with a sample to be analyzed positioned in contact with the at least one film in the well means, which is for slidably receiving the interlocking means and the sample holder along the inner surface thereof, upon the grid support with the sample positioned over the assembly grid at the marked position of primary focus; the interlocking means being for retaining the sample holder in non-rotational relationship with the assembly board and with the grid support and the assembly grid; the support means at the well means being for bearing at least the sample holder and the interlocking means;
   (f) separating the sample holder with the sample from its relationship with the interlocking means;
   (g) removing the sample holder with the sample from the well means; and
   (h) placing the sample holder with the sample into position at a spectrometer supporting plate with the sample holder aligned with the supporting plate so that the sample is positioned at the point of primary focus.

2. The method according to claims 1, 5, 6, or 10 whereby the well means is a generally circular receptacle formed by the assembly holder, and the outer holder member, the inner holder member, and the interlocking member are configured as rings and wherein the first, second, and third walls are approximately circular walls.

3. The method of claim 1, wherein step 1b includes placing the grid support into the well means, the support means also being for directly bearing the grid support; the assembly grid being spaced below the top surface of the assembly board.

4. The method according to claim 3, wherein step 1e includes the following steps:
   (a) placing first holder means into the well on top of the grid support;
   (b) placing the one film over the well means and over the first holder means;
   (c) forcing second holder means and the one film into the well means and into the first holder means, the first and second holder means including first locking means for locking the second holder means with the first holder means, the first and second holder means being for gripping the one film and creating a taut surface across the first and second holder means, the first and second holder means together comprising the sample holder;
   (d) placing the interlocking means into the well means upon the second holder means; the interlocking means and the assembly board including key means for retaining the interlocking means in non-rotational relationship with the assembly board; the interlocking means and the second holding means including alignment means for retaining the second holding means in non-rotational relationship with the interlocking means, whereby the sample holder and the sample are retained in non-rotational relationship with the grid support.
   (e) placing the sample to be analyzed onto the one film over the position of primary focus marked on the assembly grid;

5. The method according to claim 3, wherein the first holder means is an outer holder member having a first continuous generally upright wall having inner and outer surfaces, the outer surface being adapted to be slidingly received by the inner surface of the well means and having opposed first top and bottom edges and forming a first aperture aligned with the assembly grid and being positioned in contact with the top side of the grid support.

6. The method according to claim 5, wherein the second holder means is an inner holder member having a second continuous generally upright wall having inner and outer surfaces and having opposed second top and bottom edges and forming a second aperture aligned with the first aperture including a bottom face defined by the second bottom edge, the outer surface of the second wall being adapted to press against the inner surface of the first continuous wall, the second bottom edge at the same time forcing the one sheet of film downwardly into the first aperture of the outer holding member, the inner and outer holding members including locking means associated with the inner and outer surfaces for securing the inner locking member with the outer holding member so that the inner holding member is connected with the outer holding member when the first and second bottom edges come into alignment, the one film being gripped between the outer and inner surfaces of the inner and outer holder members, respectively, and forming a taut surface across the bottom face of the second aperture directly over the assembly grid when the inner holder member is fully mounted with the outer holder member, the second top edge being aligned slightly above the top edge of the outer holder member, the second top edge having flange means having opposed upper and lower sides extending over the first top edge, the flange means being in part for pressing at the lower side against the first top edge of the outer holder member when the inner holder member is fully mounted with the outer holder member; the outer and inner holder members comprising the sample holder.

7. The method according to claim 6, wherein the locking means for securing the inner holder member with the outer holder member is a snap-in mounting that includes a peripheral bead extending around the inner surface of the outer holder member spaced proximate to the first top edge and a peripheral groove extending around the outer surface of the inner holder member spaced proximate to the second top edge, the groove being adapted to receive the bead in snap-in relationship.

8. The method according to claim 7, wherein the inner surface of the outer holder member tapers inwardly from the first top edge to the first bottom edge and the outer surface of the inner holder member tapers inwardly from the peripheral cavity to the second bottom edge, the taper of the outer holder member mating with the taper of the inner locking member.

9. The method according to claim 8, wherein the outer surface of the inner holder member is chamfered inwardly around the intersection with the second bottom edge, whereby the one film is not torn during the mounting process.

10. A method according to claim 9, wherein the interlocking means is an interlocking member including a third continuous generally upright wall having inner and outer surfaces and forming a third aperture aligned with the first and second apertures, the third wall having opposed third top and bottom edges, the third bottom edge including one bottom edge portion in contact with a portion of the first top edge of the outer holder member and another bottom edge portion in contact with the upper side of the flange means of the second top edge portion of the inner holding member and with the top side of the inner holder member from which the flange extends; the outer surface of the interlocking member being slidably receivable by the inner surface of the well means.

11. A method according to claim 10, wherein the keying means means includes the assembly board forming a keyway adjoining the well means and the grid support having a first key adapted to be received by the keyway.

12. A method according to claim 11, wherein the key means includes the interlocking member having a second key adapted to be received by the keyway of the assembly board.

13. A method according to claim 12, wherein the alignment means includes the flange means of the inner holder member having at least one wide flange which forms a pair of transverse steps and the first and second top edge portions of the interlocking member forming a pair of lateral steps which are press fitted against the transverse steps of the wide flange when the interlocking member is mounted in the well.

14. A method according to claim 13, wherein the flange means further includes a narrow flange disposed generally opposite the one flange, and the alignment means further includes the bottom edge portion forming a space adjacent the second key adapted to receive the narrow flange.

15. A method according to claim 14, wherein the assembled sample holder including holder includes a first alignment mark and the sample holder support plate of the spectroscope has a second alignment mark, so that when the first mark is aligned with the second mark the sample is aligned with the primary focus of the X-Ray beam.

16. A method according to claim 15, further including the following steps:
(a) placing a second sheet of film over the well means, the inner holder member, and the interlocking member;
(b) forcing a third holder means into the well means and into the second holder member along with the second film, the third holder means and the second holder member including second locking means for holding the the third holder member in gripping relationship with the second holder member, the third holder member being for gripping the second film with the second holder member and creating a taut surface across the second holder member over the sample, the first and the second second holder members and the third holder means comprising an expanded holder member.

17. A method according to claim 16, wherein the third holder means is another inner holding member having a fourth continuous generally upright wall having inner and outer surfaces, the outer surface being adapted to be slidingly received by the inner surface of the interlocking member, the fourth wall having opposed fourth top and bottom edges and forming a fourth aperture aligned with the first, second, and third apertures, the fourth aperture including a lower face defined by the fourth bottom edge, the outer surface of the fourth wall being adapted to press fit against the inner surface of the third wall, the fourth bottom edge at the same time being adapted to force the second film downwardly into the second aperture of the inner locking member, the second film being gripped between the inner surface of the third wall and the outer surface of the fourth wall and forming the taut surface across the lower face of the fourth aperture and sandwiching the sample with the first film when the second inner locking member is mounted with the inner locking member, the another inner holder member including means for press fitting the another inner holder member into non-movable relationship with the inner locking member.

18. The method according to claim 17, wherein the means for press fitting includes the inner surface of the inner holding member being straight between the second top and bottom edges and the outer surface of the another inner holding member being tapered inwardly between the fourth top and bottom edges, the outer surface at the fourth bottom edge of the another inner holding member being adapted to be easily received at the inner surface at the second top edge of the inner holding member, and the outer surface at the fourth top edge being in tight relationship with the inner surface at the second top edge.

19. The method according to claim 18, wherein the outer surface of the another inner holder member is chamfered inwardly around the intersection with the fourth bottom edge, whereby the second film is not torn during the mounting process.

20. The method according to claim 19, wherein the outer surface of the another holder member forms air passage means between the fourth top edge and the fourth bottom edge for passing air from the fourth bottom edge between the inner surface of the inner holder member and the outer surface of the another inner holder member, so that air trapped between the first film and the second film is allowed an escape passage to the atmosphere, whereby the first and second films remain taut around the sample.

21. The method according to claim 20, further including a pair of flanged stops extending transversely outwardly from the fourth top edge, the inner surface at the third top edge forming a pair of recesses adapted to allow passage of the pair of flange stops.

22. The method according to claim 17, wherein the another inner holder member is configured as a ring and the fourth wall is an approximately circular wall.

23. The method according to claim 1, wherein step 1b includes placing the grid support into the well means at the bottom surface of the assembly holder, the assembly grid being aligned with the top surface of the assembly board, the grid, support having a bottom side opposed to the assembly grid, the bottom side being positioned upon the support surface.

24. The method according to claim 23, wherein the keying means includes the assembly board having a key extending into the well means from the bottom surface and the grid support forming a keyway adapted to receive the key.

25. The method according to claim 24, wherein the thin films are in the approximate range of 1 to several micrometers in thickness.

26. The method according to claim 25, wherein the micro-sample is in the approximate range of 0.01 micrometers to several millimeters.

27. The method according to claims 1, 5, 6, and 10, wherein the first, second and third walls are low profile walls so that beams from the X-Ray at the spectrometer not intercepted by the sample pass from the sample holder and are not intercepted by the walls.

28. The method of claim 1, wherein the sample holder is made of a resilient plastic material.

29. The method according to claims 1, 16, and 25, wherein the first and second films are thin films.

* * * * *